(12) United States Patent
Williams et al.

(10) Patent No.: US 12,256,958 B2
(45) Date of Patent: Mar. 25, 2025

(54) MEDICAL ACCESS DEVICE HAVING A GUARD ASSEMBLY

(71) Applicant: Atropos Limited, Bray (IE)

(72) Inventors: Stephen Williams, Blackrock (IE); Shane Macnally, Delgany (IE); Ronan Mcmanus, Bray (IE); Christopher D'Arcy, Dublin (IE); Frank Bonadio, Bray (IE); Olwen Coughlan, Dublin (IE)

(73) Assignee: Atropos Limited, Bray (IE)

( * ) Notice: Subject to any disclaimer, the term of this patent is extended or adjusted under 35 U.S.C. 154(b) by 469 days.

(21) Appl. No.: 17/443,700

(22) Filed: Jul. 27, 2021

(65) Prior Publication Data

US 2022/0031355 A1 Feb. 3, 2022
US 2023/0255662 A9 Aug. 17, 2023

Related U.S. Application Data

(60) Provisional application No. 63/057,633, filed on Jul. 28, 2020.

(51) Int. Cl.
*A61B 17/02* (2006.01)
*A61B 17/34* (2006.01)
*A61B 90/00* (2016.01)

(52) U.S. Cl.
CPC ...... *A61B 17/3423* (2013.01); *A61B 17/0218* (2013.01); *A61B 2017/0225* (2013.01); *A61B 2017/3429* (2013.01); *A61B 2017/3452* (2013.01); *A61B 2090/08021* (2016.02)

(58) Field of Classification Search
None
See application file for complete search history.

(56) References Cited

U.S. PATENT DOCUMENTS

| | | | | |
|---|---|---|---|---|
| 2004/0173218 A1* | 9/2004 | Yamada | ............. | A61B 17/3423 606/213 |
| 2005/0288558 A1* | 12/2005 | Ewers | ................ | A61B 17/0293 600/206 |
| 2011/0054260 A1* | 3/2011 | Albrecht | ............ | A61B 17/3462 600/208 |
| 2012/0130183 A1* | 5/2012 | Barnes | ............... | A61B 17/3423 600/206 |

(Continued)

FOREIGN PATENT DOCUMENTS

| | | | |
|---|---|---|---|
| AU | 2011 203 189 A1 | | 7/2011 |
| EP | 2 226 023 A1 | | 9/2010 |

(Continued)

OTHER PUBLICATIONS

International Search Report and Written Opinion in corresponding Application No. PCT/EP2021/071083, dated Jan. 31, 2023, (10 pages).

(Continued)

*Primary Examiner* — Jan Christopher L Merene
(74) *Attorney, Agent, or Firm* — Bookoff McAndrews, PLLC

(57) ABSTRACT

A medical device to protect a body opening, the medical device including a sleeve having a proximal end and a distal end a proximal ring attached to the proximal end of the sleeve, and a guard assembly located a distal end of the sleeve.

19 Claims, 33 Drawing Sheets

(56) References Cited

U.S. PATENT DOCUMENTS

| | | | |
|---|---|---|---|
| 2015/0238179 A1* | 8/2015 | Kanehira | A61B 17/0293 600/204 |
| 2016/0262794 A1 | 9/2016 | Wachli et al. | |
| 2017/0056065 A1 | 3/2017 | Do et al. | |
| 2017/0224321 A1 | 8/2017 | Kessler et al. | |
| 2017/0325800 A1 | 11/2017 | Prior | |
| 2017/0340866 A1 | 11/2017 | Richard | |
| 2022/0015803 A1* | 1/2022 | Baril | A61B 17/3423 |

FOREIGN PATENT DOCUMENTS

| | | |
|---|---|---|
| WO | 2014116889 A1 | 7/2014 |
| WO | 2014207077 A1 | 12/2014 |
| WO | 2019/094502 A1 | 5/2019 |
| WO | 2019/206537 A1 | 10/2019 |

OTHER PUBLICATIONS https://www.youtube.com/watch?v=Mm7bSYezuB4.

* cited by examiner

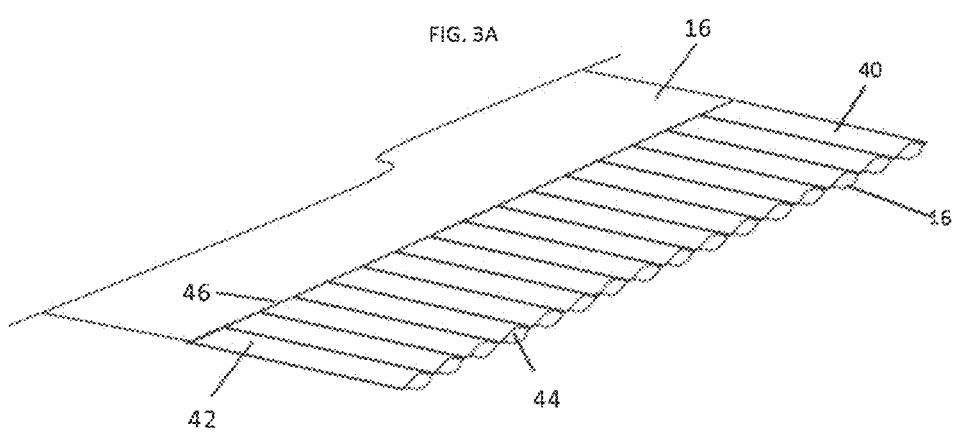
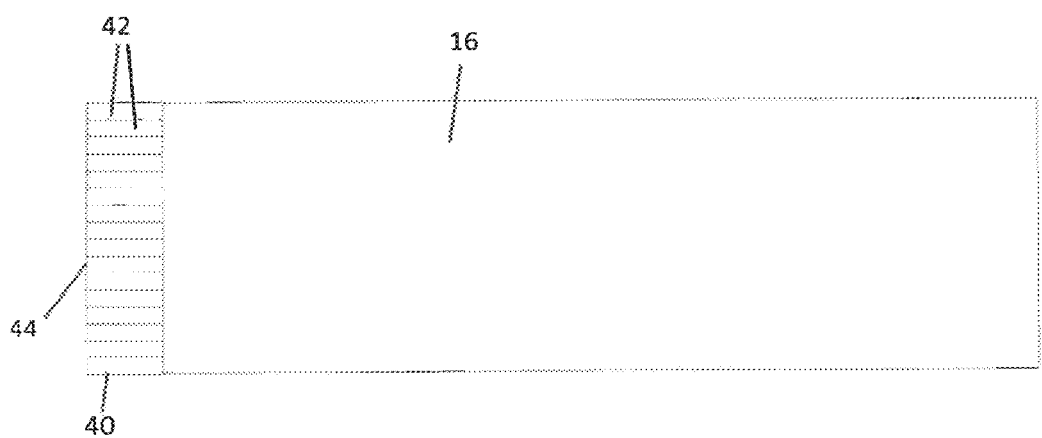

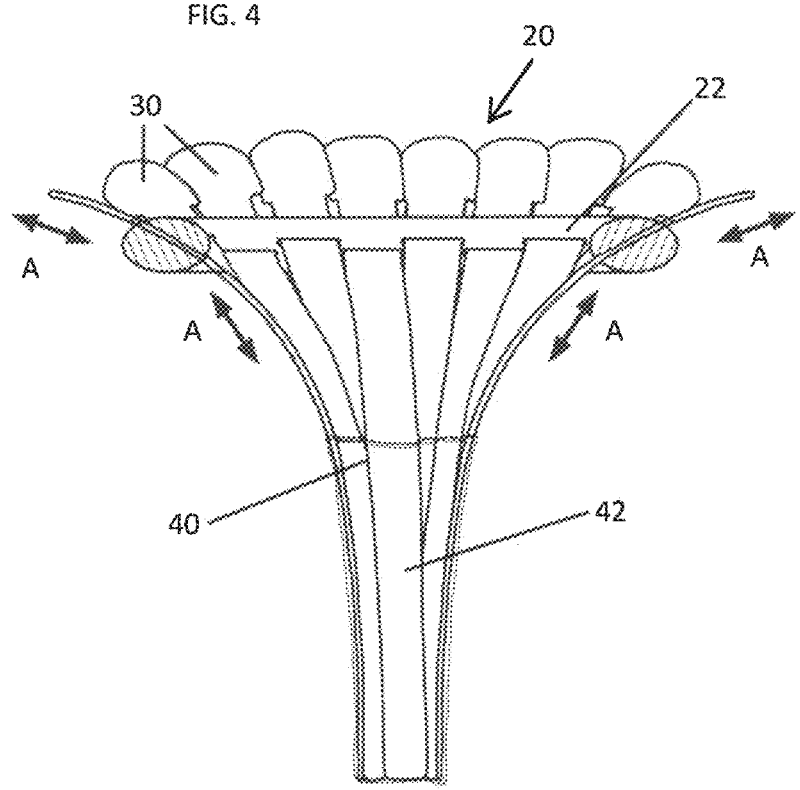

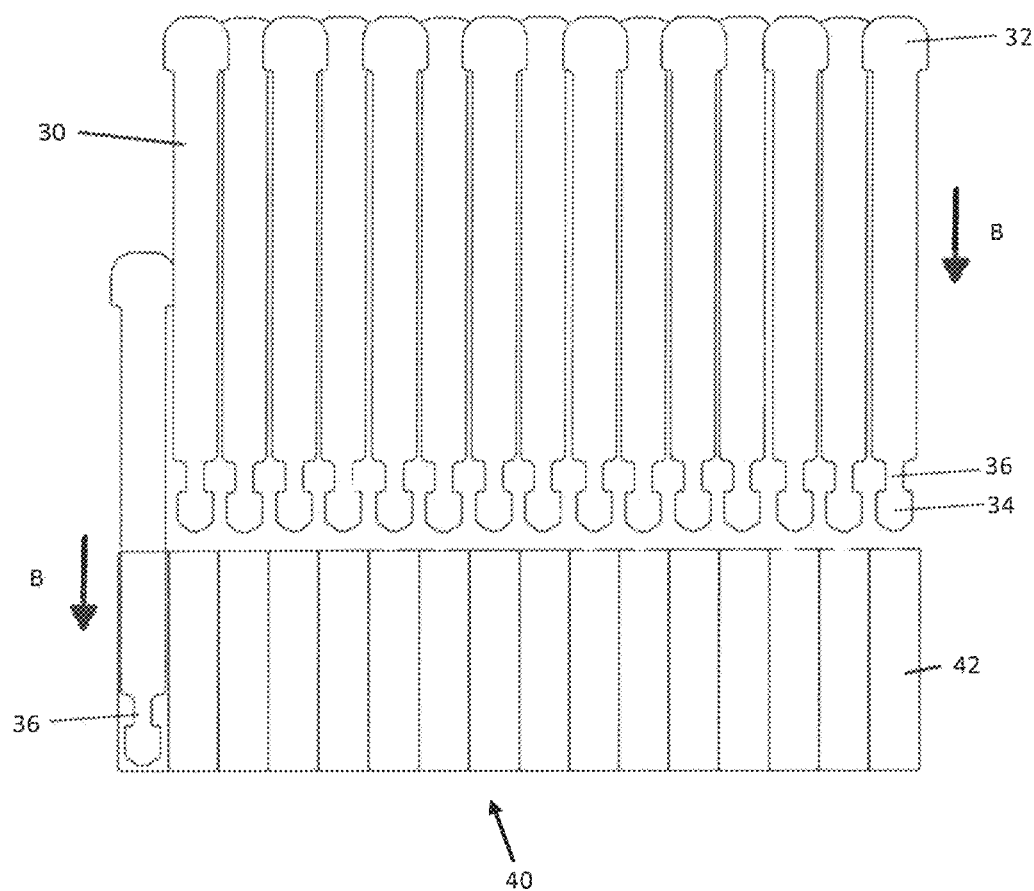

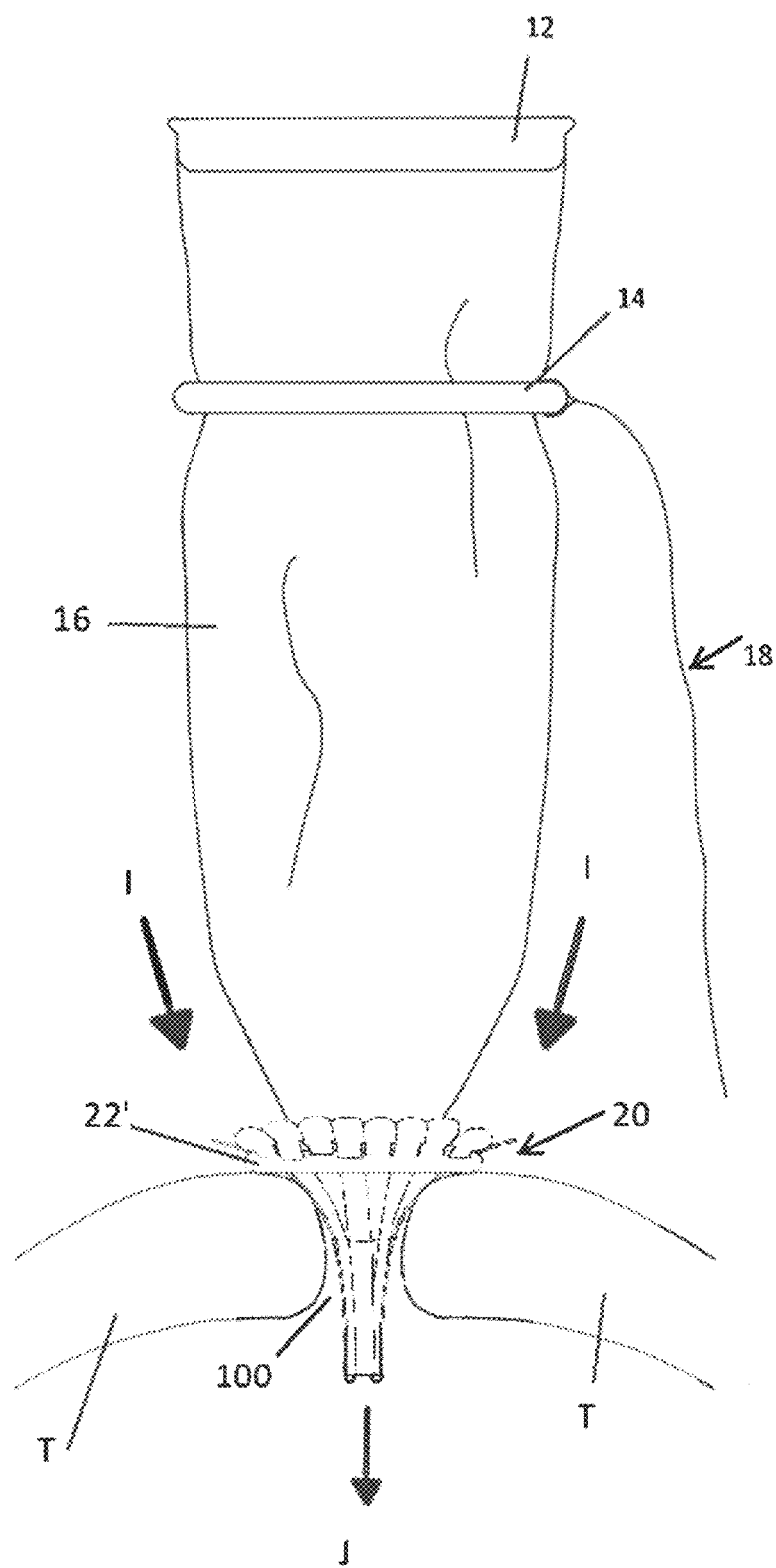

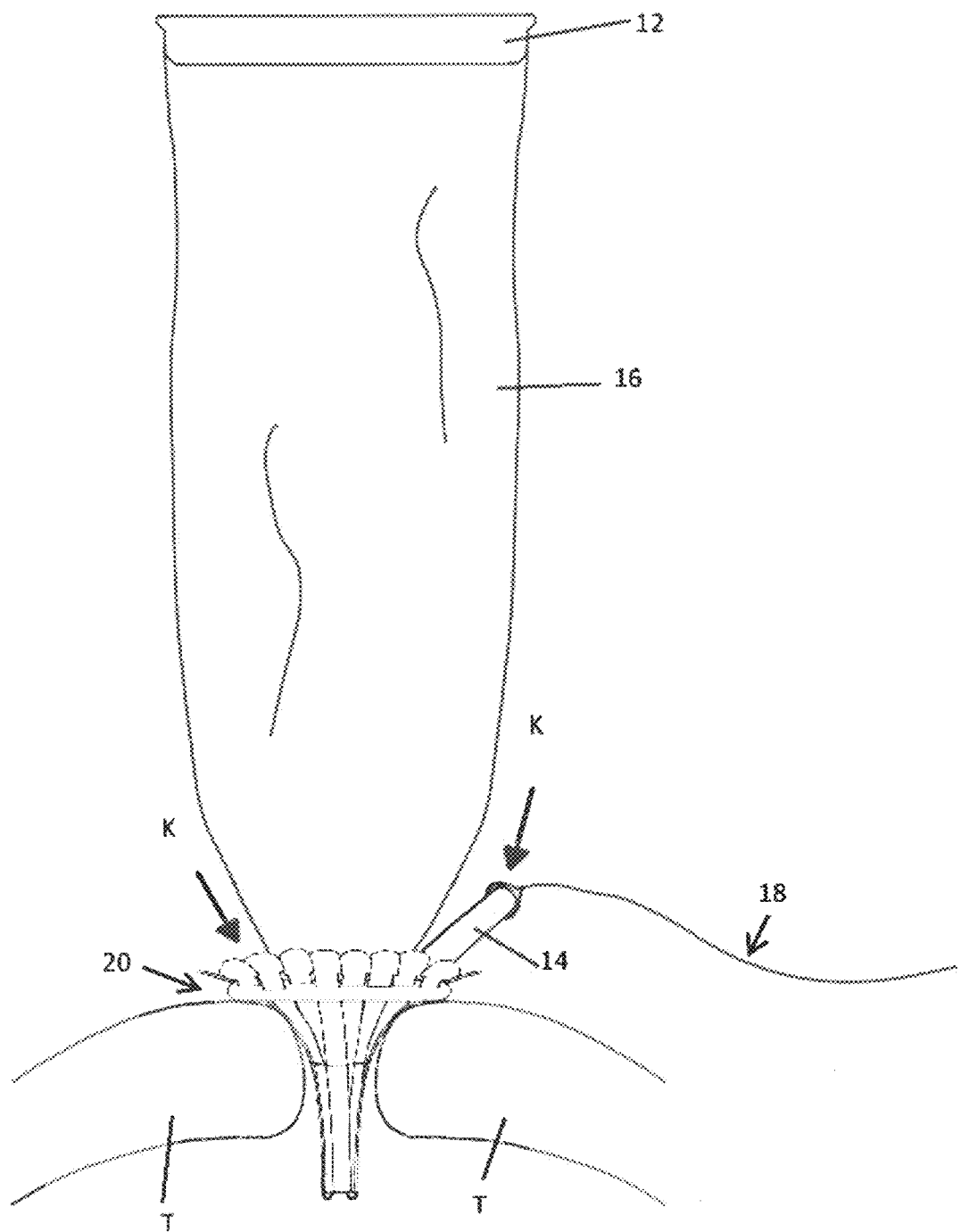

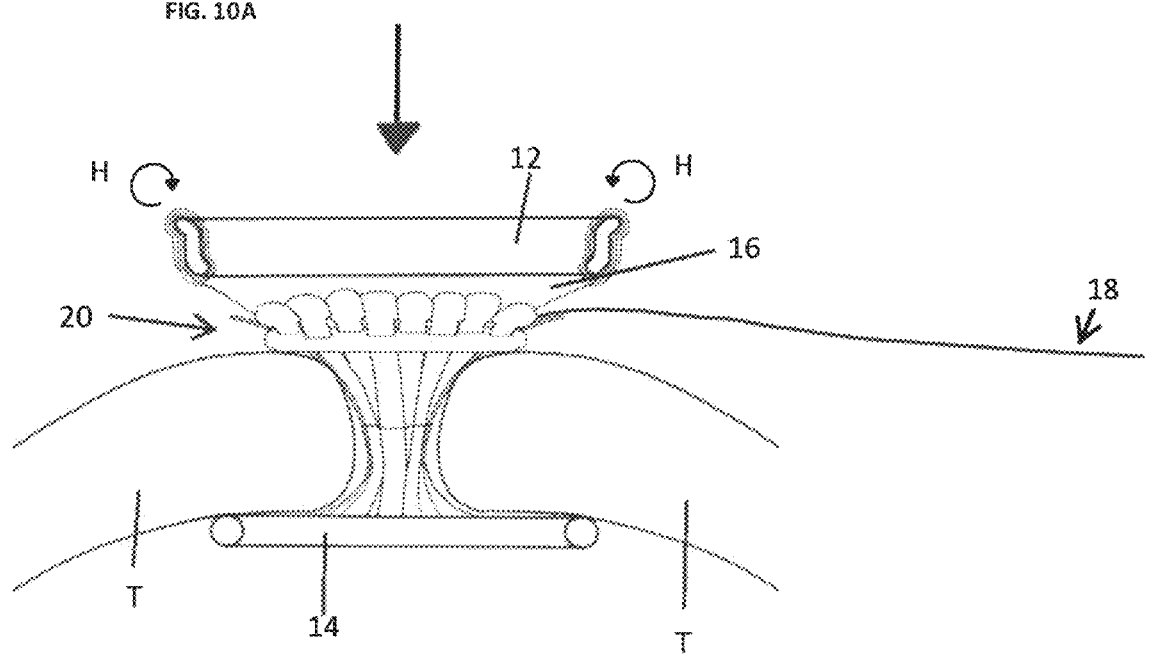
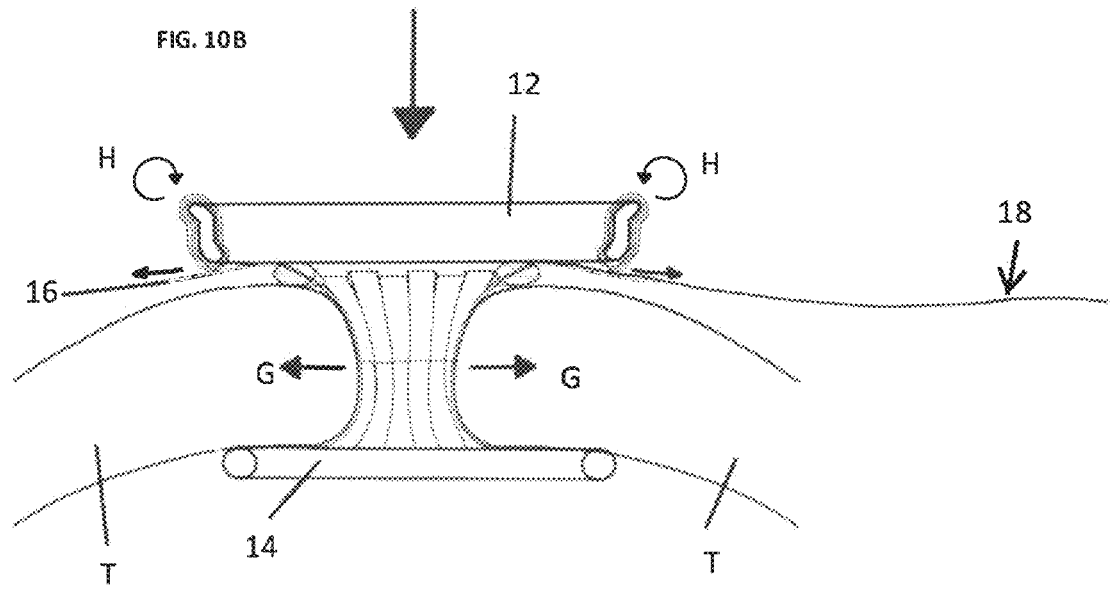

FIG. 13A
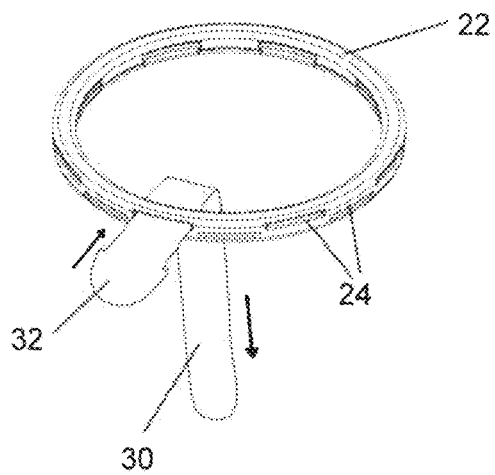
FIG. 13B
FIG. 13D
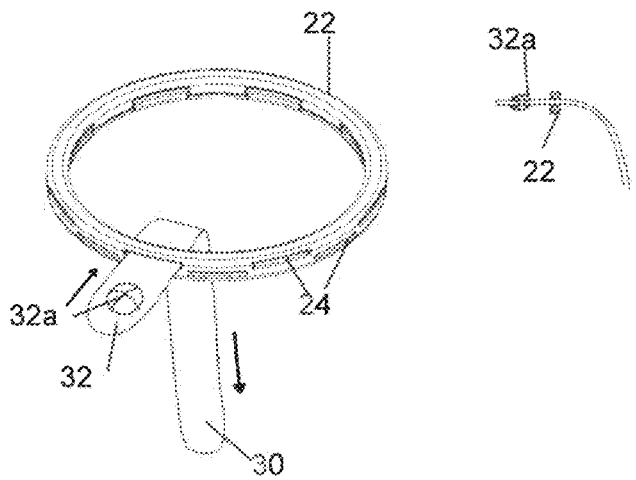
FIG. 13C
FIG. 13E
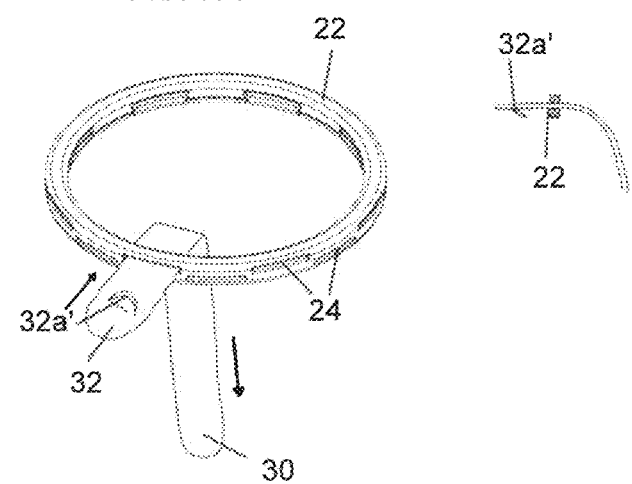

FIG. 15A
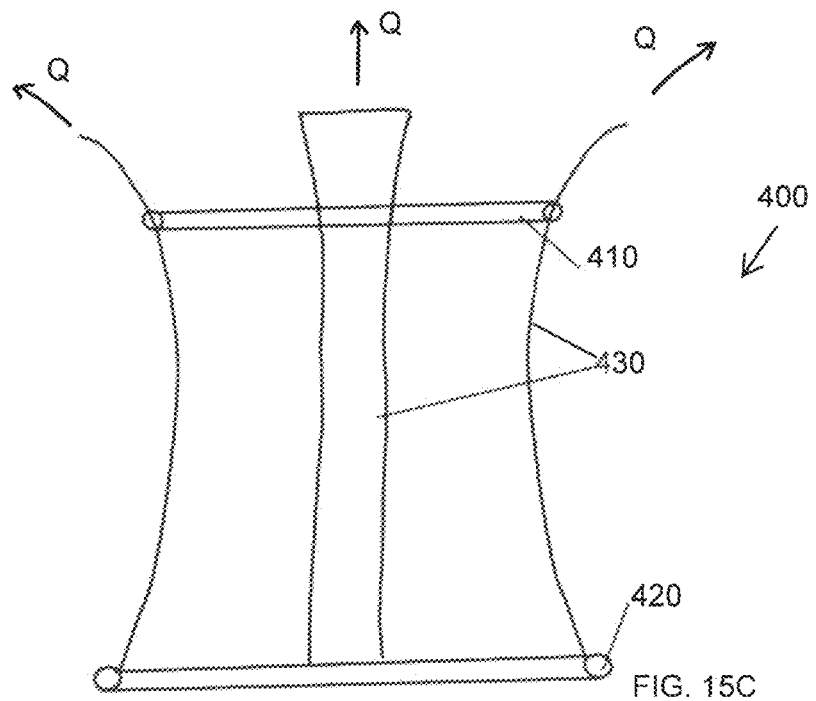
FIG. 15B
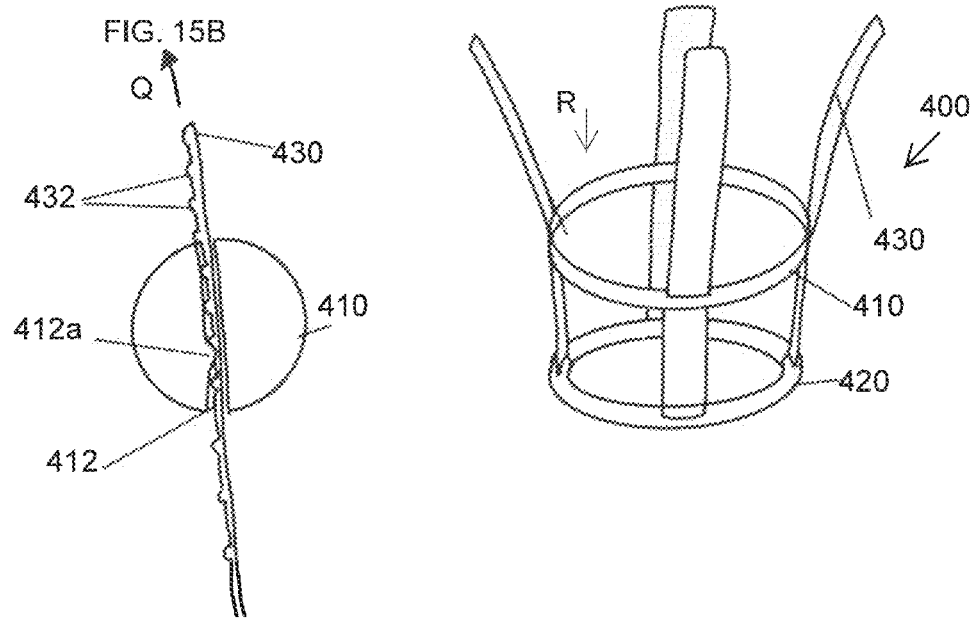
FIG. 15C

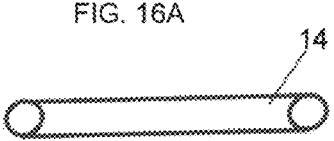
FIG. 16A
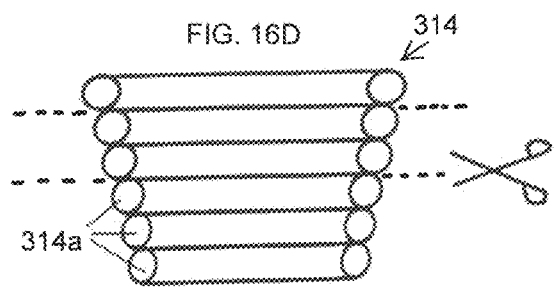
FIG. 16D
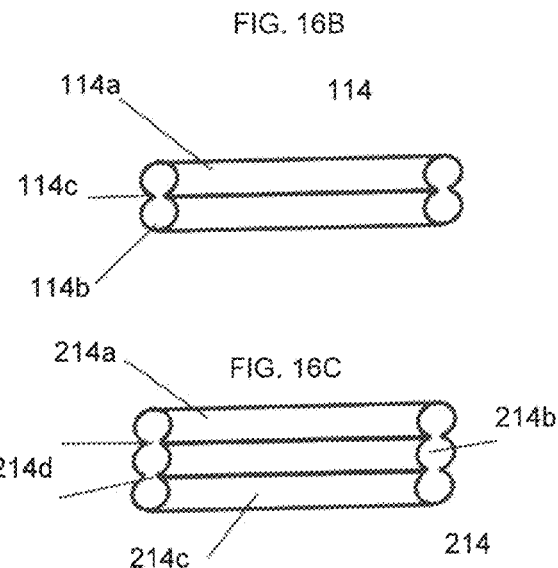
FIG. 16B
FIG. 16C
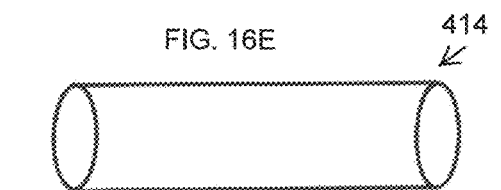
FIG. 16E
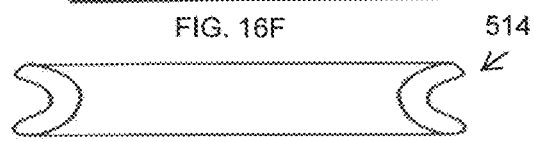
FIG. 16F
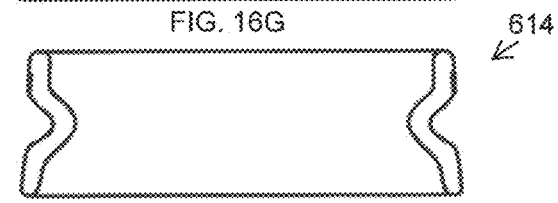
FIG. 16G
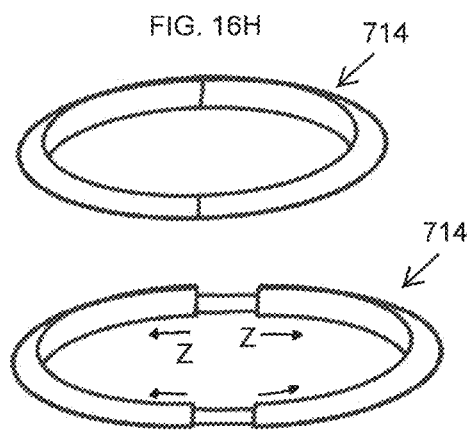
FIG. 16H
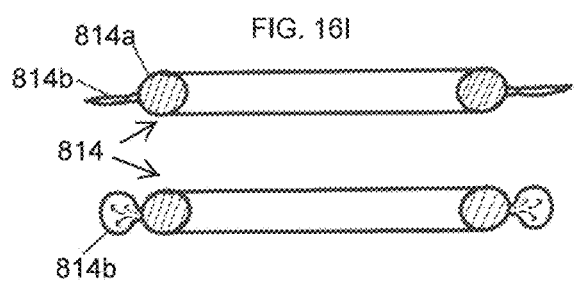
FIG. 16I
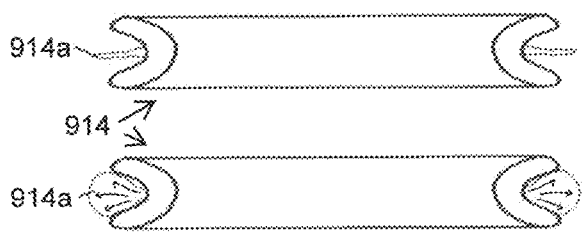
FIG. 16J

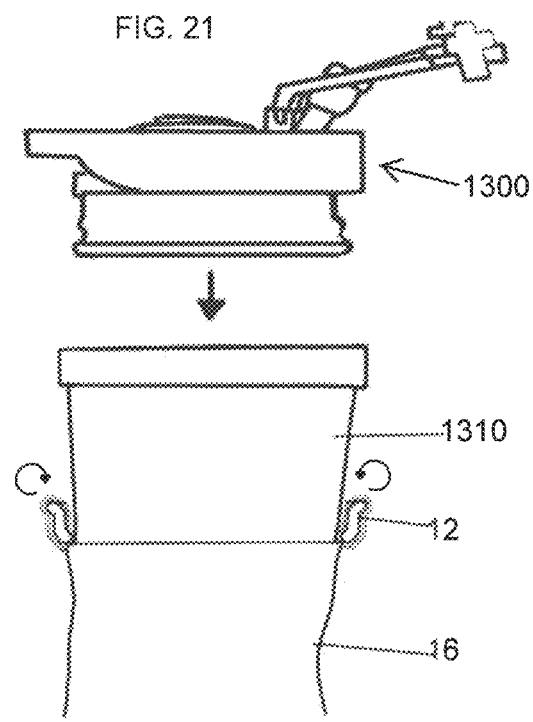

MEDICAL ACCESS DEVICE HAVING A GUARD ASSEMBLY

CROSS-REFERENCE TO RELATED APPLICATIONS

This application claims the benefit of priority of U.S. Provisional Application No. 63/057,633 filed Jul. 28, 2020, the contents of which are incorporated herein in its entirety.

TECHNICAL FIELD

The present disclosure relates generally to medical systems and devices for accessing a body cavity, and more particularly, to methods and devices for accessing and protecting an opening in a body during a medical procedure.

BACKGROUND

Medical devices are used with a body to perform various medical procedures. These procedures may access the body via an opening, e.g., an incision or a natural orifice (e.g., transanal, tranvaginal, transabdominal, or any other natural opening or incision formed in the body), and may include using tools that may damage the body opening. For example, instruments such as scalpels or other sharp objects, or instruments including catheters or other similar devices may contact the body opening and damage the tissue surrounding the body opening via a friction force. These drawbacks may cause trauma to the patient and/or may cause complications with associated medical procedures. Accordingly, it may be desirable to ensure that the body openings, and the surrounding tissues, are protected during the medical procedures to prevent such damage. The present disclosure may solve one or more of these problems or other problems in the art. The scope of the disclosure, however, is defined by the attached claims and not the ability to solve a specific problem.

SUMMARY OF THE DISCLOSURE

According to an aspect, a medical device for protecting a body opening includes a sleeve having a proximal end and a distal end, a proximal ring attached to the proximal end of the sleeve, and a guard assembly located a distal end of the sleeve.

The guard assembly may include a plurality of elongate members, and wherein a portion of each of the elongate members may be secured to the distal end of the sleeve.

The distal end of the sleeve may include a plurality of pockets, and each of the elongate members may be secured within a corresponding pocket of the plurality of pockets.

The guard assembly may include a guard ring having a plurality of apertures, wherein each of the elongate members may extend through one aperture from the plurality of apertures, and wherein the plurality of elongate members may be configured to slide within a corresponding aperture from the plurality of apertures.

A portion of the sleeve may extend proximally through an aperture in the guard ring.

The device may further comprise a distal ring, wherein the distal ring may be movable relative to the sleeve and the guard, and wherein the distal ring may be movable to a position distal to a distal-most end of the guard assembly.

According to an aspect, a medical device configured to protect a body opening includes a sleeve having a proximal end and a distal end, and a guard assembly located at the distal end of the sleeve, wherein the guard assembly includes a guard ring and a plurality of petals, wherein the plurality of petals are movably connected to the guard ring.

The guard ring may include a plurality of apertures, and wherein one petal from the plurality of petals may be disposed within a corresponding aperture of the plurality of apertures.

A portion of the sleeve may be received within the guard ring.

According to an aspect, a medical device configured to protect a body opening includes a sleeve having a proximal end and a distal end, a guard assembly having a plurality of petals, and a plurality of pockets formed at the distal end of the sleeve, wherein each petal of the plurality of petals is secured within a corresponding pocket of the plurality of pockets.

A width at a distal end of each petal may be less than a width of each petal at the proximal end, and wherein a connection member in each of the plurality of pockets may cooperate with the distal end of a corresponding petal to fix the petal into the corresponding pocket.

According to an aspect, a medical device configured to protect a body opening in a deployed configuration includes a sleeve having a proximal end and a distal end, a proximal ring attached to the proximal end of the sleeve, a guard assembly located at the distal end of the sleeve, and a distal ring, wherein the distal ring is movable relative to the sleeve and the guard, and wherein the distal ring is disposed at a distal-most end of the guard assembly in the deployed configuration.

The distal ring may be configured to be moved between a first position, in which at least a portion of the distal ring may be disposed outside the body, and a second position, in which the distal ring may be disposed within the body.

A portion of the sleeve may be received within the distal ring.

According to an aspect, a method of retracting a body opening includes inserting a medical device into the body opening, the medical device including a sleeve, a proximal ring attached to a proximal end of the sleeve, a guard assembly attached to a distal end of the sleeve, and a distal ring, moving the distal ring from a first position, wherein at least a portion of the distal ring is disposed outside the body, to a second position, in which the distal ring is disposed entirely inside the body, and moving the proximal ring distally to urge a portion of the sleeve and guard radially outwardly within the body opening.

Moving the proximal ring further may include rolling the proximal ring proximally to shorten a distance of sleeve between the proximal ring and the distal ring.

The guard assembly may include a guard ring and a plurality of petals, and moving of the proximal ring may move the petals with respect to the guard ring.

The method may further include inserting an auxiliary device into the body opening before the medical device is inserted into the body opening.

According to an aspect, a medical device configured to protect a body opening includes a sleeve having a proximal end and a distal end, a proximal ring attached to the proximal end of the sleeve, a distal ring received about a portion of the sleeve, and a guard assembly located a distal end of the sleeve, the guard assembly including a guard ring, a plurality of petals movably coupled to the guard ring, and a plurality of petal pockets receiving the plurality of petals.

The sleeve may form a portion of the guard assembly.

A portion of the sleeve may be received within the guard assembly.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 3A and 3B are views of a sleeve of the medical access device of FIG. 1A;

FIG. 4 is a view of a guard assembly of the medical access device of FIG. 1A;

FIGS. 7A, 7B, and 7C are views of petals of the guard system of FIG. 4;

FIGS. 9A, 9B, 9C, 9D, 9E, and 9F are views illustrating an insertion of the medical device of FIG. 1A into a body;

FIGS. 10A, 10B, 10C, 10D, and 10E are views illustrating a movement of the proximal ring of the medical device of FIG. 1A;

FIGS. 13A, 13B, 13C, 13D, and 13E are views illustrating petals of the medical device of FIG. 1A;

FIGS. 15A, 15B, 15C, and 15D are views illustrating a medical device according to another embodiment;

FIGS. 16A, 16B, 16C, 16D, 16E, 16F, 16G, 16H, 16I, and 16J are views illustrating distal rings according to an embodiment;

FIG. 21 is a view illustrating a cap according to an embodiment;

DETAILED DESCRIPTION

Figure 1A:
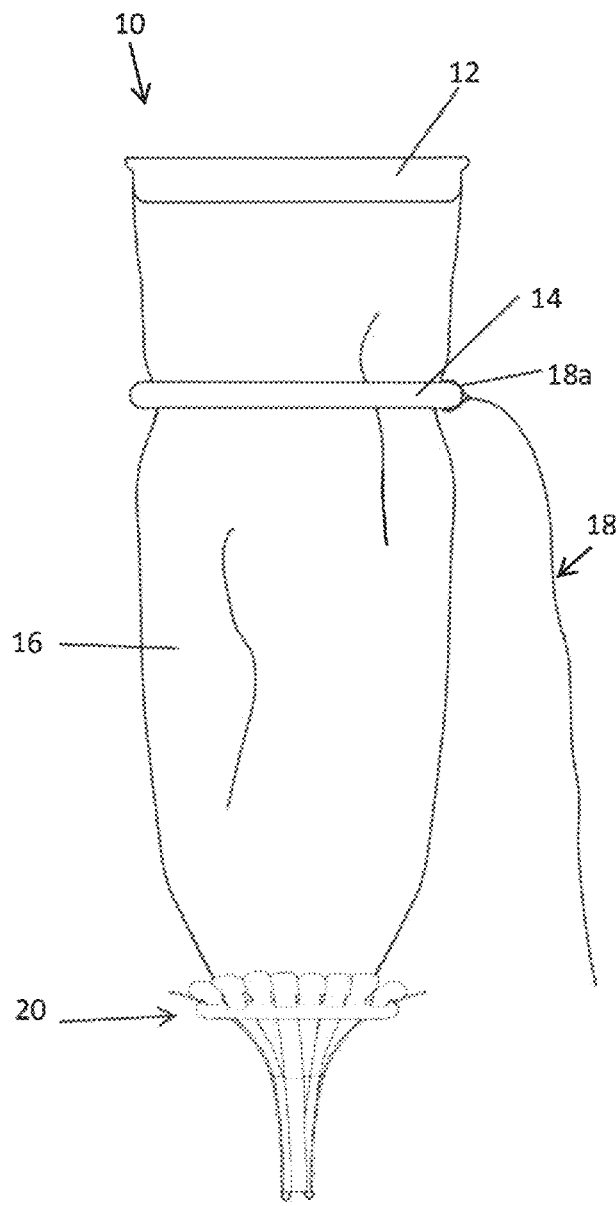
FIGS. 1A and 1B are schematics of a medical access device according to an embodiment of the present disclosure.

The present disclosure is now described with reference to exemplary medical access devices that may be used in accessing the interior of the body. However, it should be noted that reference to any particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions/regions/ends of a device and/or its components are referred to as proximal and distal ends/regions. It should be noted that the term "proximal," is intended to refer to ends/regions closer to a user of the disclosed device (e.g., outside the body of the patient), and the term "distal," used herein to refer to ends/regions farther away from the user of the disclosed device (e.g., inside the body of the patient). Similarly, extends "distally" indicates that a component extends in a distal direction, and extends "proximally" indicates that a component extends in a proximal direction. Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1B:
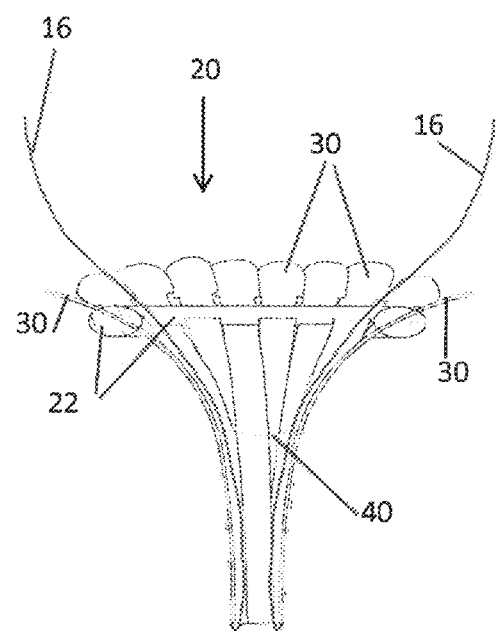

Referring to FIGS. 1A and 1B, a medical device in the form of a medical access device 10 according to an embodiment is shown. Access device 10 may include a proximal ring 12, a sleeve 16 attached to proximal ring 12, and a guard assembly 20 at a distal end of sleeve 16. A distal ring 14 may be disposed about and may move relative to sleeve 16, proximal ring 12, and guard assembly 20. As shown in FIG. 1B, guard assembly 20 may include a plurality of circumferentially arranged, longitudinally extending elongate guard members or petals 30 slidably received within a guard ring 22 and secured within a petal pockets portion 40 at a distal end of the sleeve 16.

Distal ring 14 may be a flexible ring formed of a rubber, a resin, or the like. Distal ring 14 may be generally circular in cross-section and form a generally torus or O-ring shape, but the cross-section may take other shapes. A diameter of distal ring 14 may be approximately 50 mm to approximately 150 mm, but is not limited to this size. A tether 18 may be connected to distal ring 14 by a tether connection 18a. Tether 18 may have a length sufficient to extend proximally from a body opening when distal ring 14 is disposed within the body, as will be described below. Tether 18 may be formed of any appropriate material.

Figure 2A:
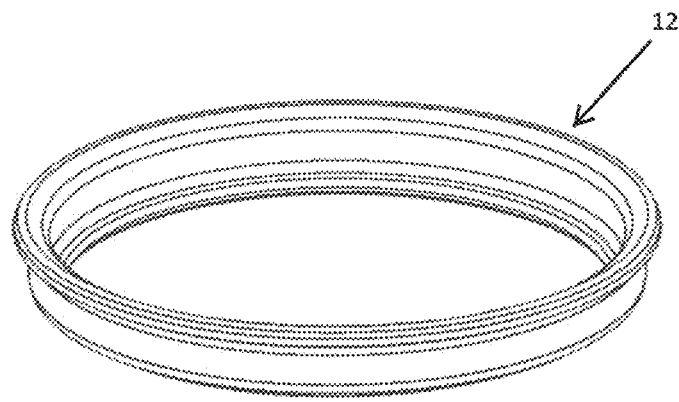
FIGS. 2A, 2B, and 2C are views of a proximal ring of the medical access device of FIG. 1A.
Figure 2B:
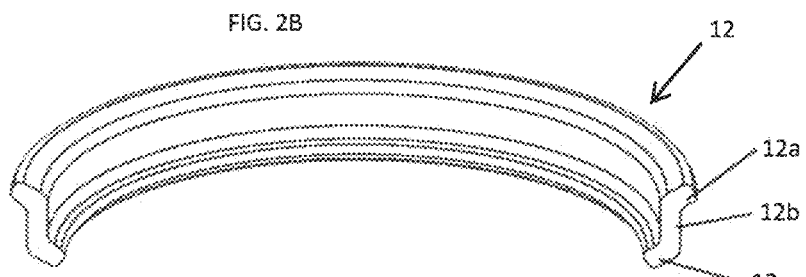
Figure 2C:
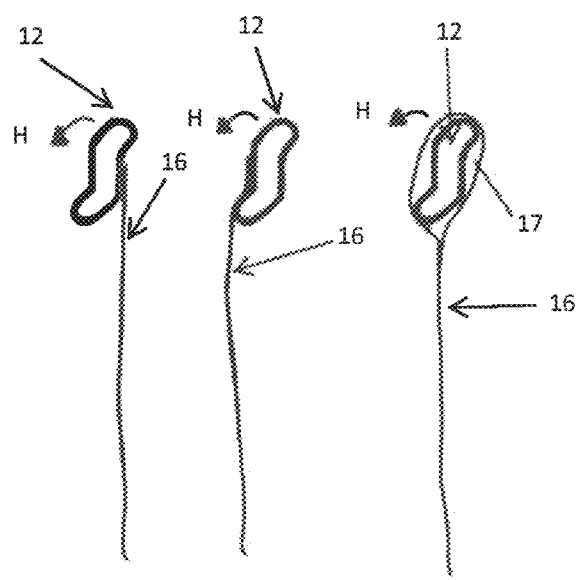

Proximal ring 12 is shown in detail in FIGS. 2A-2C. As shown in FIG. 2A, proximal ring 12 may be solid and continuous about its circumference. FIG. 2B shows a cross-section of proximal ring 12 forming a generally "S" shape having a first end section 12a angled radially outward from a central section 12b, and a second end section 12c extending radially inward from central section 12b. Thus, the first end section 12a and the second end section 12b extend in opposite directions. Central section 12c may include a cross-section with parallel sides extending parallel to a longitudinal axis of the access device 10. Proximal ring 12 may be formed in an alternative shape. Proximal ring 12 may be flexible and may be formed of any suitable material, including a medical grade polyurethane, rubber, resin, or similar flexible material to facilitate rolling of proximal ring 12. Proximal ring 12 may be larger than guard ring 22 and larger than an opening in the body in which medical device 10 is inserted. For example, proximal ring 12 may be approximately 50 mm to approximately 150 mm, or approximately 100 mm. However, the diameter of proximal ring 12 is not limited thereto, and may be any size suitable for use assisting with the retraction of a body opening.

FIG. 2C illustrates sleeve 16 attached to proximal ring 12 in various alternative examples. As a first example, a proximal end of sleeve 16 may be fixedly attached to a radially outer surface of proximal ring 12. According to another example, the proximal end of sleeve 16 may be fixedly attached to a radially inner surface of proximal ring 12. According to yet another example, a channel 17 may be formed at a proximal end of sleeve 16, and proximal ring 12 may be received and/or secured within channel 17. In each example, proximal ring 12 may be rolled in the direction indicated by arrows H in FIG. 2C to cause sleeve 16 to wrap about proximal ring 12 and thus decrease a length or distance between proximal ring 12 and distal ring 14, as will be described in more detail below.

With reference back to FIG. 1A, sleeve 16 may be a continuous piece of material extending from proximal ring 12 to a distal end of guard assembly 20. Sleeve 16 may be flexible and may conform to a shape and a size of a body opening 100 (see, e.g., FIG. 5A). For example, sleeve 16 may be a medical grade material, including a polyurethane film, a Kevlar or other cut or puncture resistant material, or the like. Sleeve 16 may be any length suitable for insertion into the body opening, with a remainder extending proximal from the body opening. For example, sleeve 16 may be approximately 100 mm to approximately 350 mm, or approximately 250 mm. However, the length of sleeve 16 may vary based on the medical procedure and/or the area of the body being accessed. As will be explained in more detail below, the distal end of sleeve 16 may form a portion of guard assembly 20.

Figure 9B:
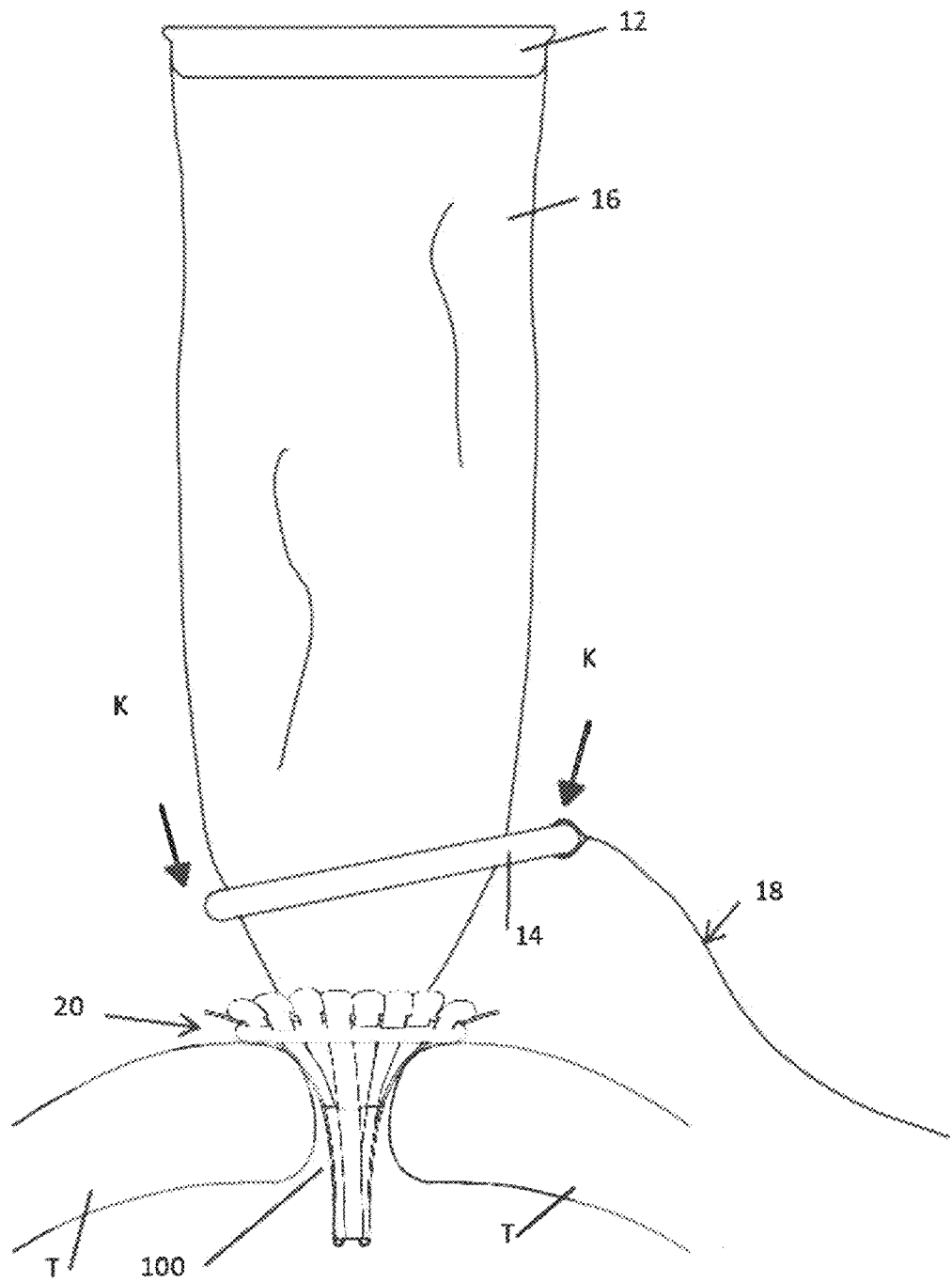
Figure 9D:
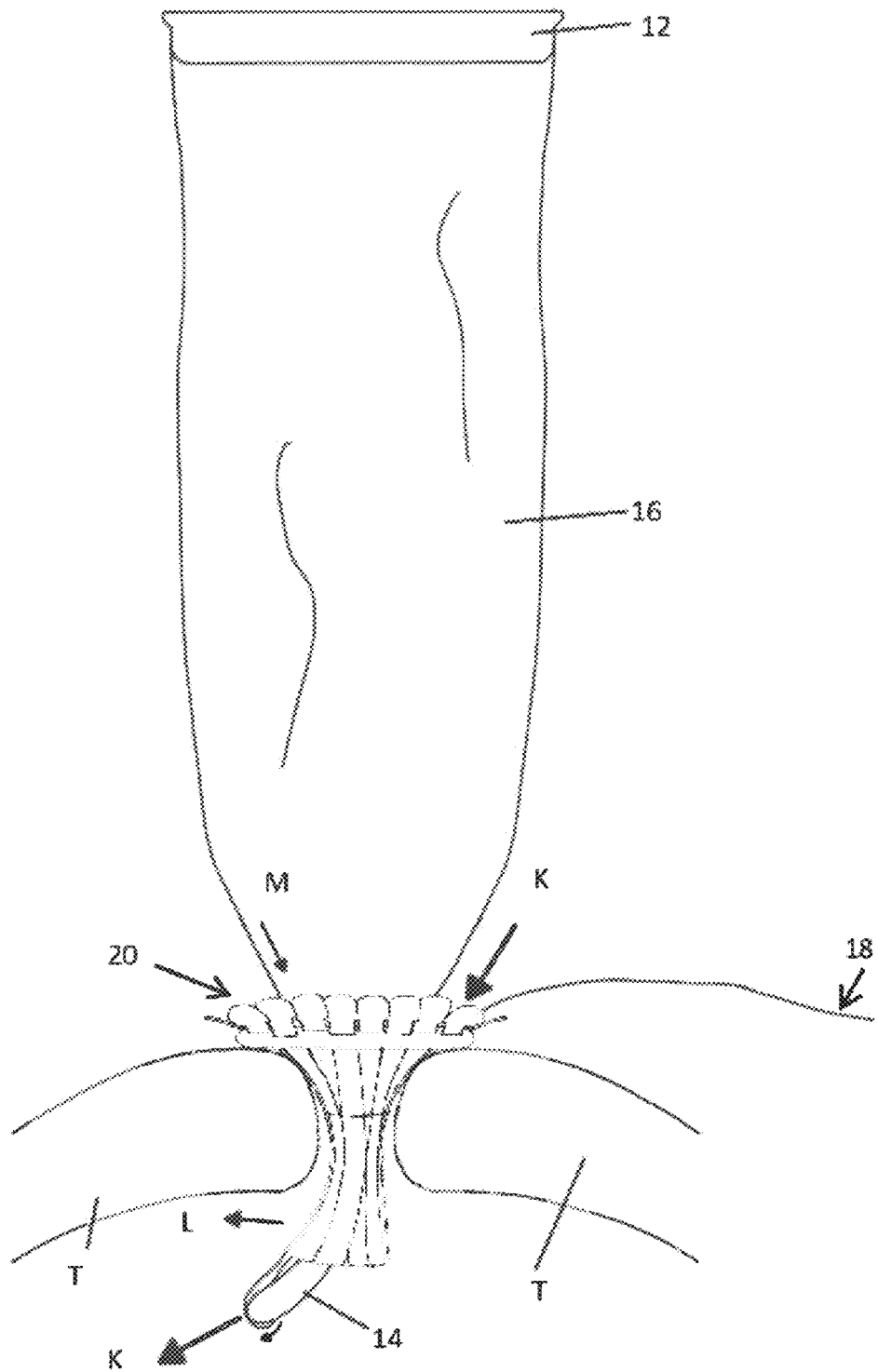
Figure 9E:
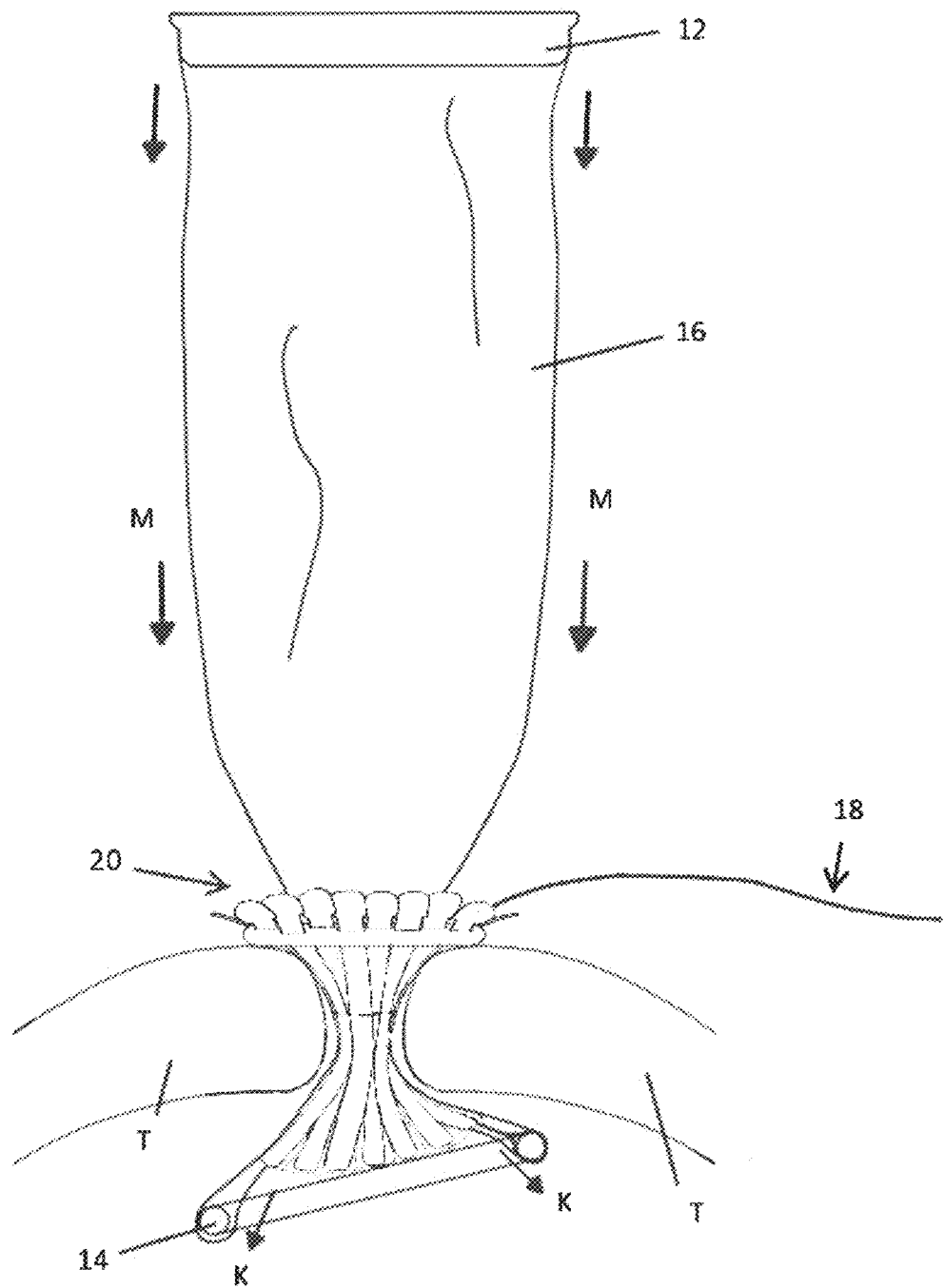
Figure 9F:
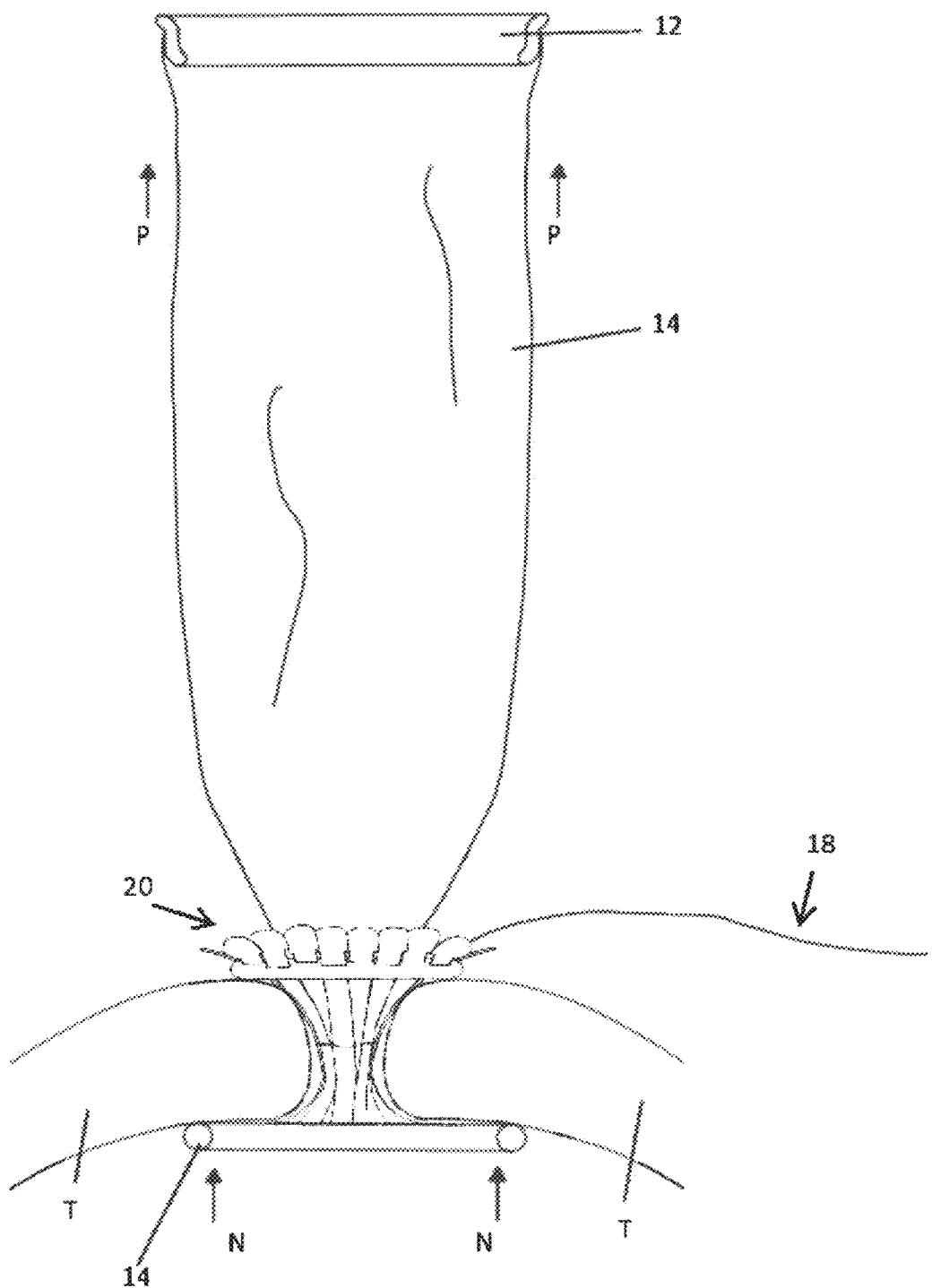

FIGS. 3A and 3B illustrate a petal pockets portion 40 of guard assembly 20 formed by a distal end of sleeve 16. The petal pocket portion 40 may include a plurality of petal pockets, channels or slots 42 formed at the distal end of sleeve 16. As will be explained in more detail below, the petal pockets 42 may be sized to receive and secure petals 30 of guard assembly 20. As shown in FIG. 3A, in an unassembled configuration of access device 10, the plurality of petal pockets 42 have an open distal end 44 and a closed proximal end 46. The open distal end 44 of petal pocket portion 40 forms a distal-most end of sleeve 16 in the unassembled configuration. Petal pocket portion 40 may be formed by folding a length of sleeve 16 at the distal end of sleeve 16 back toward the proximal end of sleeve 16. Then, the distal end of sleeve 16 is sealed with adhesive or laser welded to form each of the petal pockets 42, with a final step of cutting the distal-most end of the sleeve 16 to form the open ends 44 of the petal pockets 42. Alternatively, the petal pocket portion 40 could be formed by a separate sleeve portion sealed or welded to the distal end of the sleeve 16 to form the petal pocket portion 40. The separate sleeve portion may be the same material or a different material as a material of sleeve 16. Petal pockets 42 may have a length based, at least in part, on a size and shape of the opening in the body. For example, if a medical procedure is performed at an area having a small tissue T thickness and a large body cavity, the length of petal pockets 42 may be short enough such that petal pockets 42 do not contact guard ring 22 in such a way as to cause an obstruction. Petal pockets 42 may have a width approximately equal to or greater than a width of petals 30 contained therein. According to an example, there may be sixteen petal pockets 42, corresponding to sixteen petals 30. However, it will be understood that the number of petal pockets 42 and the number of petals 30 may change based on, e.g., a size of the sleeve or a width of petals 30. As best shown in FIG. 1B, in the assembled configuration of access device 10, sleeve 16 may be inverted, or pulled through a central opening of guard assembly 20. Thus, in this assembled configuration, the distal end of sleeve 16 includes the petal pocket portion 40 surrounding a portion of sleeve 16, and the open ends 44 of petal pockets 42 are located proximal to the closed ends 46. Further, the closed ends 46 of pockets 42 are at the distal-most end of sleeve 16. As will be explained in more detail below, in this assembled configuration, the distal ring 14 may positioned between the inner surface of the petal pocket portion 40 and an outer portion of sleeve 16 at a distal-most end of sleeve 16 (FIG. 9F). It will also be understood that petals 30 may be attached directly to sleeve 16, e.g., via welding, such that petal pockets 42 are not necessary.

Figure 5A:
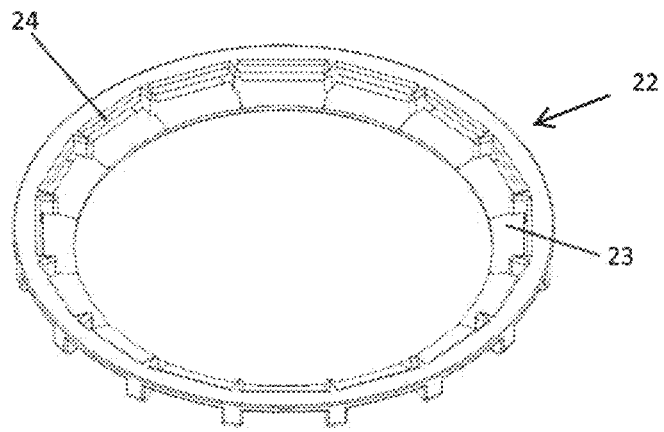
FIGS. 5A, 5B, and 5C are views of a guard ring of the guard device of FIG. 4.
Figure 5B:
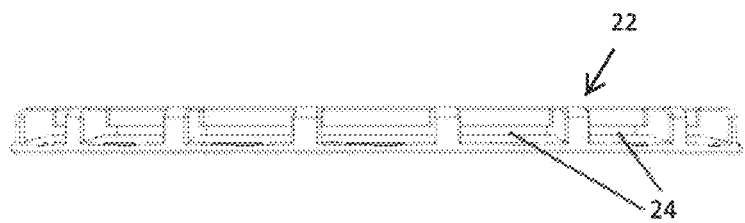
Figure 5C:
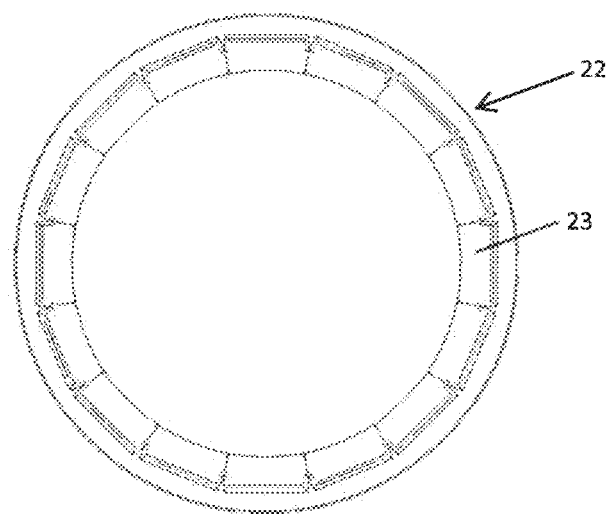

FIG. 4 illustrates an embodiment of guard assembly 20 with a portion of sleeve 16 omitted. As noted above, guard assembly 20 includes petals 30 and a guard ring 22. Petals 30 may be elongate members having a generally rectangular cross-section. As shown in FIG. 4, petals 30 may slide within guard ring 22 in the direction indicated by arrows A. For example, as shown in the embodiment of FIGS. 5A-5C, guard ring 22 may include a plurality of apertures or slots 24 radially disposed about guard ring 22. Each aperture 24 may be sized to receive a single petal 30. As petals 30 move relative to guard ring 22, petals 30 may slide within apertures 24. Apertures 24 may have a shape approximately equal to a cross-sectional shape of petals 30. For example, apertures 24 may be rectangular in shape, and may be sized to have a height and width approximately equal to or greater than the thickness and width of each of petals 30. According to an example, guard ring 22 may include sixteen apertures 24, corresponding to sixteen petals 30. However, it will be understood that the number of apertures 24 and the number of petals 30 may change based on, e.g., a size of the body opening or a width of petals 30. In some examples, a protrusion 23 extends from an inner side of each aperture 24 toward a central axis of guard ring 22. Protrusions 23 may be sloped from the inner side of each aperture 24 in a distal direction. Protrusions 23 may form a guide ramp for petals 30 and may reduce a stress on petals 30 as guard ring 22 moves relative to petals 30.

Figure 6A:
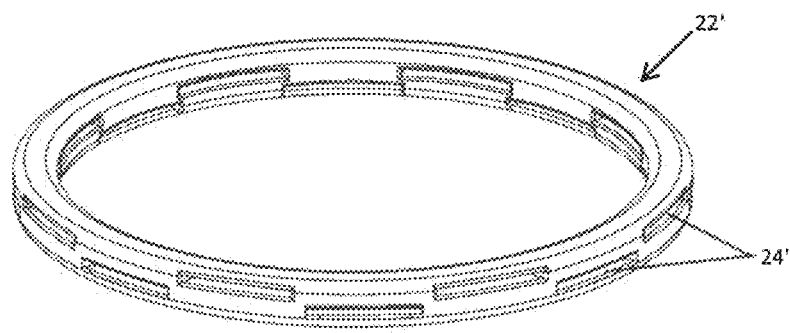
FIGS. 6A, 6B, and 6C are views of another guard ring of the guard system of FIG. 4, according to another embodiment.
Figure 6B:
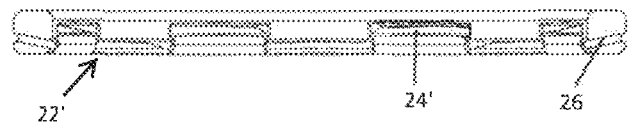
Figure 6C:
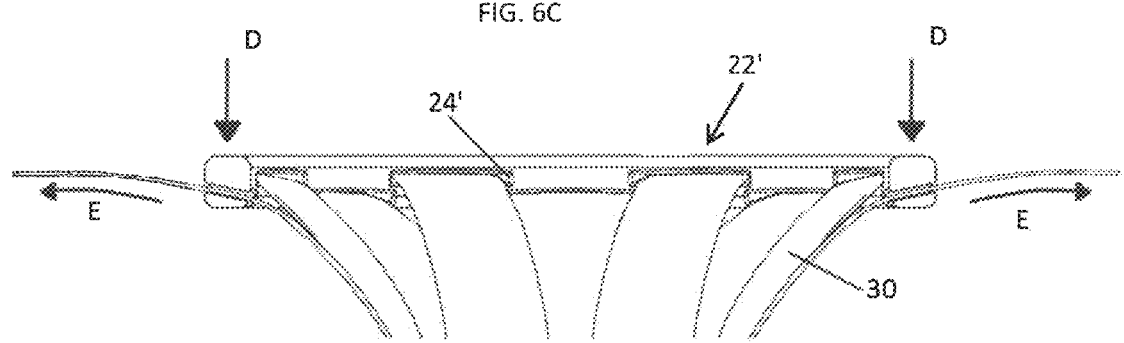

A guard ring 22' according to another embodiment is shown in FIGS. 6A-6C. Guard ring 22' includes apertures 24' distally arranged about guard ring 22'. Adjacent apertures 24' may be offset in a proximal-distal direction. For example, a first aperture 24' may be arranged in guard ring 22' closer to a distal end of guard ring 22', and adjacent apertures 24' may be arranged in guard ring 22' closer to a proximal end of guard ring 22'. The arrangement of apertures 24' may prevent petals 30 from bunching up as guard ring 22' moves relative to petals 30. An inner surface 26 of each of apertures 24' may be sloped such that a radially outer surface of aperture 24' is more proximal than a radially inner surface of aperture 24', as shown by the cross-section of guard ring 22' in FIG. 6C. This arrangement may guide petals 30 as petals 30 move relative to guard ring 22', similar to the guidance protrusions 23 provided in guard ring 22.

Figure 7B:
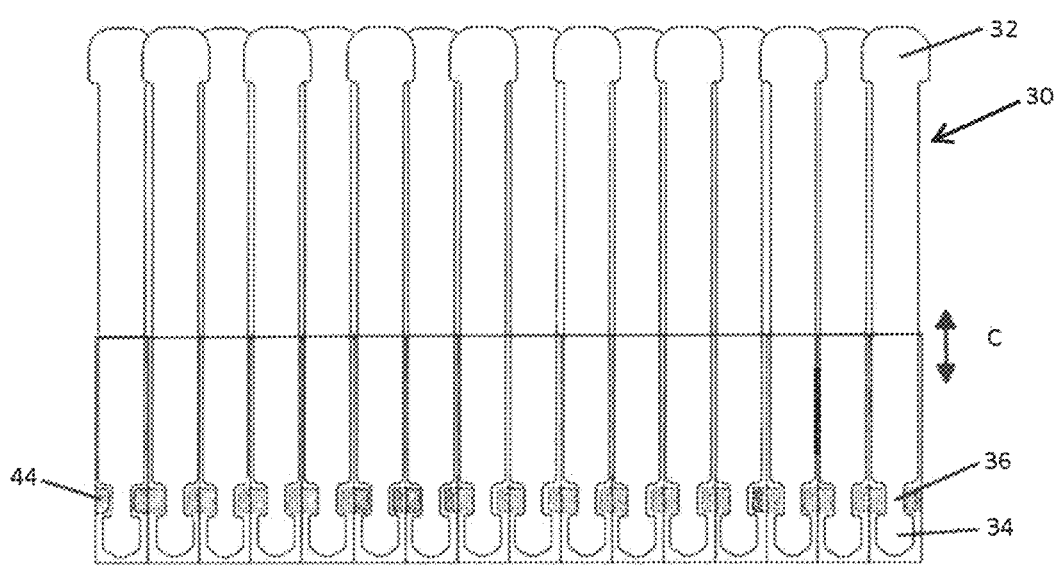
Figure 7C:
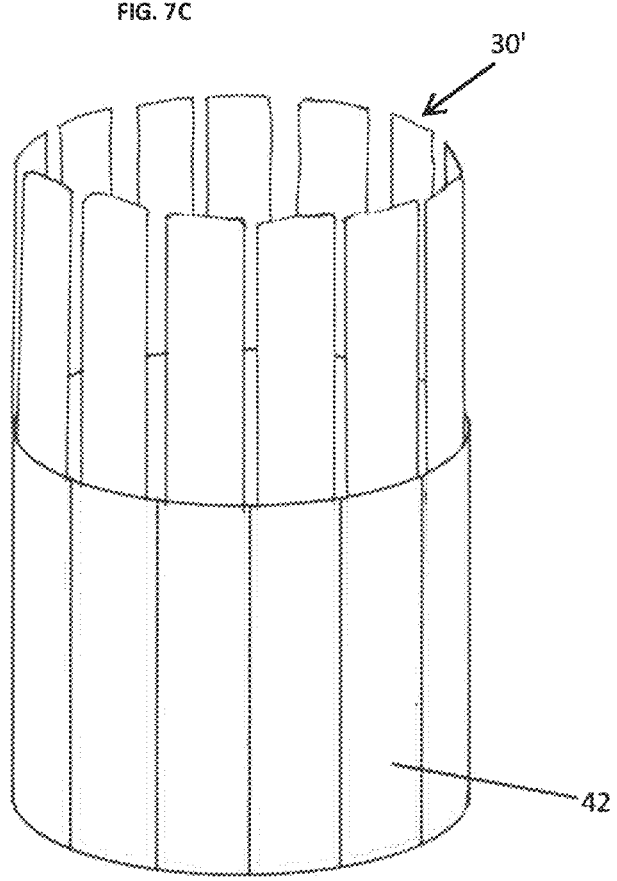

Reference is now made to FIGS. 7A-7C, which illustrate petals 30 and petal pocket portion 40 of guide assembly 20. Petals 30 may be fixed within petal pockets 42 so that the petals 30 stay secured within pockets 42 during use of the access device 10. As noted above, petals 30 may be generally rectangular in shape, having a longer length (from a proximal end 32 to a distal end 34) than a width that is normal to the length. However, other shapes than rectangular may be used. Petals 30 may be flexible and/or bendable, and formed of a polyester material, a plastic material, or the like. As shown in FIG. 7B, when the petals 30 are secured within petal pockets 42, a majority of the petal 30 extends proximal of the petal pocket 42. This also enables each petal 30 and corresponding petal pocket 42 to move freely relative to adjacent petals 30 based on a size and a shape of the opening in the body.

As shown in FIG. 7A, petals 30 may each have a proximal end 32 which is wider than the distal end 34 of petals 30. For example, proximal end 32 of petals 30 may have a width greater than a width of apertures 24 or 24'. In this manner, as petals 30 slide relative to guard rings 22 or 22', the wider proximal end 32 may prevent guard rings 22 or 22' from sliding off petals 30. Alternative embodiments of proximal end 32 of petal 30 are described with reference to FIGS. 13A-13C herein. Distal end 34 of petals 30 may include a grooved portion 36 having, for example, a pair of grooves which may be used to fasten petal 30 within petal pocket 42. For example, distal end 34 of petal 30 may be inserted into petal pocket 42 in the direction indicated by arrow B in FIG. 7A. Referring to FIG. 7B, a connection portion 44 may be formed within one or more petal pockets 42 by melting, laser welding, or like method to deform sleeve 16 within the grooves of grooved portion 36 of to fix petals 30 within petal pockets 42. Alternatively, connection portions 44 may be preformed within petal pockets 42, e.g., using a raised piece of material. This may allow the petals 30 to be inserted into pockets 42 and past the connection portions 44 (with increased force and the tapered distal-most end of the petal 30), yet make it difficult to remove the petals based on the connection portions and transversely extending ends of the grooves of grooved portion 36. It will be understood that petals 30 may be fixed within petal pockets 42 in alternative manners, e.g., via direct adhesive, laser welding, or the like.

According to another embodiment, FIG. 7C illustrates a plurality of petals 30' disposed within respective petal pockets 42. Petals 30' may be formed without an enlarged proximal end 32 and/or without distal end 34. For example, each petal 30' may be a single rectangular piece of material fixed within respective petal pockets 42 via, e.g., laser welding, adhesive, or the like.

As described herein, proximal end 32 of petals 30 may be enlarged to prevent guard rings 22 or 22' from sliding off petals 30. For example, as shown in FIG. 13A, proximal end 32 of petal 30 may have a larger cross-section than a distal end of petal 30, which may prevent petal 30 from sliding through slots 24 of guard ring 22 (or slots 24' of guard ring 22' shown in FIGS. 6A-6C). According to another embodiment shown in FIGS. 13B and 13D, proximal end 32 may include a rivet 32a (or other raised surface) which may increase a thickness proximal end 32 of petal 30. A size of rivet 32a may be larger than slot 24 of guard ring 22 (or slot 24' of guard ring 22' in FIGS. 6A-6C) and may prevent petal 30 from sliding through slots 24 or 24'. Yet another embodiment of proximal end 32 of petal 30 is shown in FIGS. 13C and 13E. A tab 32a' may be formed in proximal end 32. Tab 32a' may extend downwards relative to petal 30, as shown in FIGS. 13C and 13E, or upwards relative to petal 30. Tab 32a' may contact a radially outer surface of guard ring 22 (or guard ring 22') and may prevent proximal end 32 of petal 30 from sliding through slots 24 or 24'.

A method of inserting access device 10 will be described with reference to FIGS. 9A-9F. Guard assembly 20 may be inserted into a body opening 100 as shown in FIG. 9A. For example, the distal end of guard assembly 20 may be inserted through an incision in a tissue T of the body, a natural orifice, or any other body opening 100 in the direction indicated by arrow J. As guard assembly 20 is advanced distally into opening 100, proximal end of sleeve 16 is maintained outside the body. A distal end of guard assembly 20 may be advanced distally into opening 100 such that guard ring 22 rests against an outer surface of tissue T surrounding opening 100. While reference is made to guard ring 22, it will be understood that guard ring 22' may be used in a similar manner as guard ring 22.

Once guard assembly 20 is positioned within opening 100, distal ring 14 may be moved distally along the outside of sleeve 16, as shown by arrows K in FIG. 9B. As shown in FIGS. 9B and 9C, distal ring 14 may continue to be moved distally in the direction indicated by arrows K. Distal ring 14 may be pinched or otherwise deformed and moved into body opening 100 via the space created by the inverted portion of sleeve 16 and the inner surface of petal pocket portion 40. As distal ring 14 continues to move into the body, distal ring 14 pulls a portion of sleeve 16 into the body opening (see arrow M, as shown in FIG. 9D), such that a portion of sleeve 16 is distal of guard assembly 20 (see FIG. 9E). Once the distal ring is distally beyond the opening 100, the distal ring may expand to an approximately circular shape, and in doing so, causing the distal end of guard assembly 20, including the distal end 34 of petals 30, to move radially outward within the body, as shown in FIG. 9E.

Figure 10C:
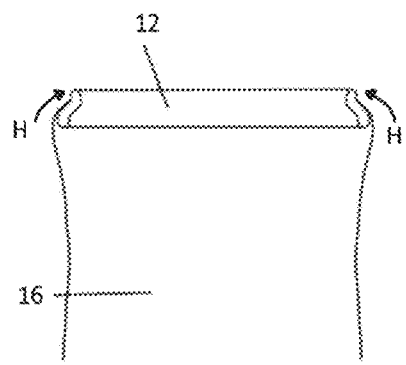
Figure 10D:
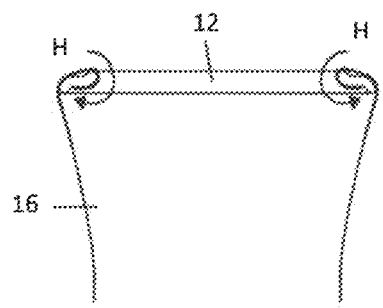
Figure 10E:
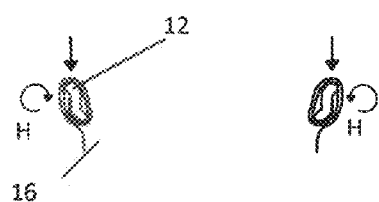

Once distal ring 14 is expanded within the body, the user may pull proximal ring 12 in the proximal direction, as indicated by arrows P in FIG. 9F. Movement of sleeve 16 in the direction indicated by arrows P urges distal ring 14 in the proximal direction, as indicated by arrows N, and against tissue T within the body. With reference to FIGS. 10A-10E, the user may subsequently roll proximal ring 12 in the direction indicated by arrows H. Rolling proximal ring 12 may cause the sleeve 16 disposed outside the body to gather around proximal ring 12, as shown in FIGS. 10C-10E. As the user continues to roll proximal ring 12 in the direction indicated by arrows H, the excess material of sleeve 16 gathers around proximal ring 12 and proximal ring 12 approaches body opening 100. As further shown in FIG. 10B, continued rolling of proximal ring 12 urges the distal ring 14 against the distal surface of tissue T, effectively seating, anchoring or "locking" guard assembly 20 within opening 100. Continued rolling of proximal ring 12 shortens the amount of sleeve 16 between the proximal ring 12 and distal ring 14, thereby causing the sleeve 16 to exert a generally radial force G on opening 100 to enlarge the opening 100. This shortening of the distance between the proximal ring 12 and distal ring 14 also urges guard ring 22 against a proximal surface of tissue T, and causes proximal ends 32 of petals 30 to slide radially outward from guard ring 22. The continued rolling of proximal ring 12, and in particular the radial force G from sleeve 16, causes the distal end of petals 30 that are disposed within opening 100 and in petal pocket portion 40, to press radially expand against tissue T. Due to the shortening of the distance between the proximal ring 12 and distal ring 14, the petals slide proximally through guard ring 22 so that less of the distal end of the petals 30 is located within opening 100. Further the radial expansion of opening 100 causes the petals 30 to move circumferentially so that there is less circumferential overlap of the petals 30. Finally, since the proximal end 32 of petals 30 extend outside the body, radial expansion of guard assembly 20 may be assisted by an operator pulling on individual petals 30 of the guard assembly 20.

Figure 8A:
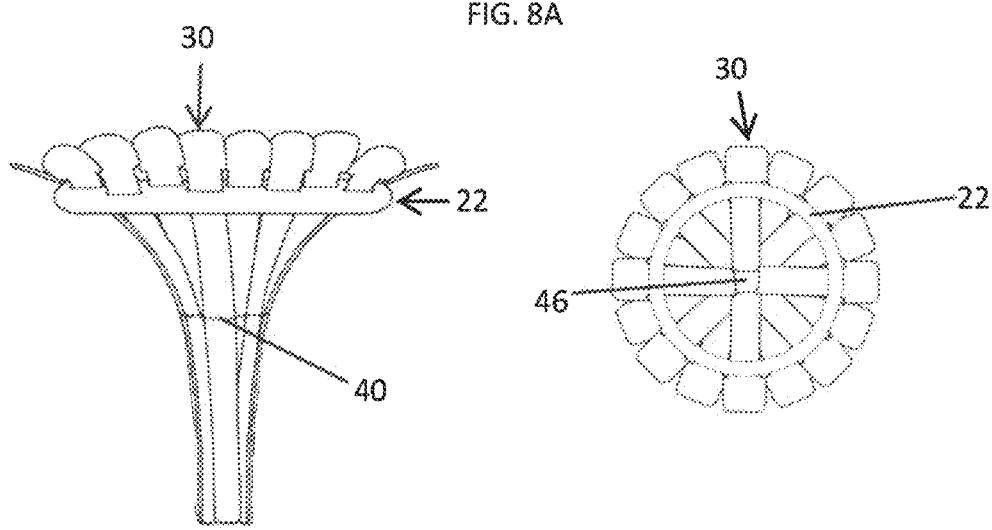
FIGS. 8A, 8B, and 8C are views illustrating a movement of the petals of the guard system of FIG. 4.
Figure 8B:
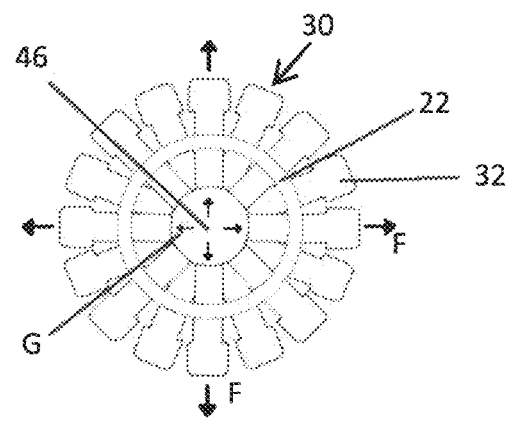
Figure 8C:
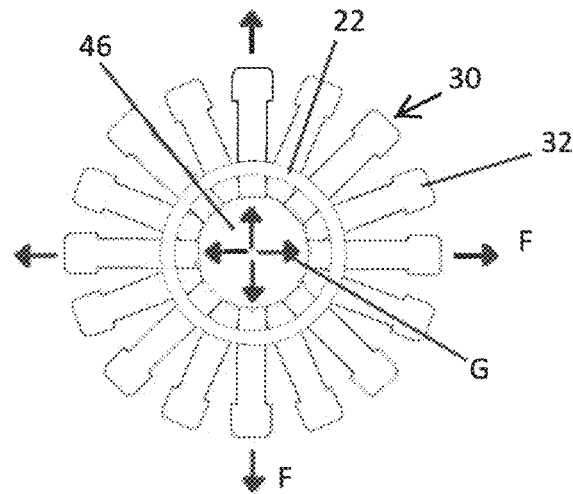

The movement of the petals is shown in FIGS. 8A-8C, which illustrate movement of petals 30 within guard ring 22. In a first state, proximal ends 32 of petals 22 may be adjacent and/or may rest against guard ring 22. Petals 30 may significantly overlap with each other at the distal end. A guard aperture 46 may be formed at the confluence of the distal ends of petals 30, as shown in FIG. 8A. When proximal ring is rolled to shorten the distance of the sleeve 16 between proximal ring 12 and distal ring 14, petals 30 may be urged against a tissue of the body opening 100 (FIG. 9A). As the sleeve 16 further urges petals 30 against the tissue (indicated by arrow G. FIGS. 8B and 8C), the tissue and petals 30 are urged radially outward, increasing a diameter of guard aperture 46. As petals 30 are capable of sliding within and relative to guard ring 22, proximal ends 32 of petals 30 move radially outward in the direction indicated by arrow F. Guard aperture 46 may provide access to a body cavity via the body opening, while providing protection to the tissue of the body opening. The radially expansion of the guard aperture 46, and the associated radial expansion of the distal end of sleeve 16 within the opening, provide a protected access opening through which tools, devices, and other medical instruments may be inserted into opening 100. Further, since petals 30 still cover all or generally all of the opening 100 in the radially expanded configuration, petals 30 may provide substantially full circumferential protection to tissue T from being cut by sharp instruments, friction forces causes by inserting or removing medical instruments via opening 100, or other trauma that may be caused by inserting and/or removing medical devices via opening 100. Once medical device 10 is disposed within opening 100, medical instruments or other devices may be inserted and/or removed via opening 100 to perform medical procedures.

Figure 23A:
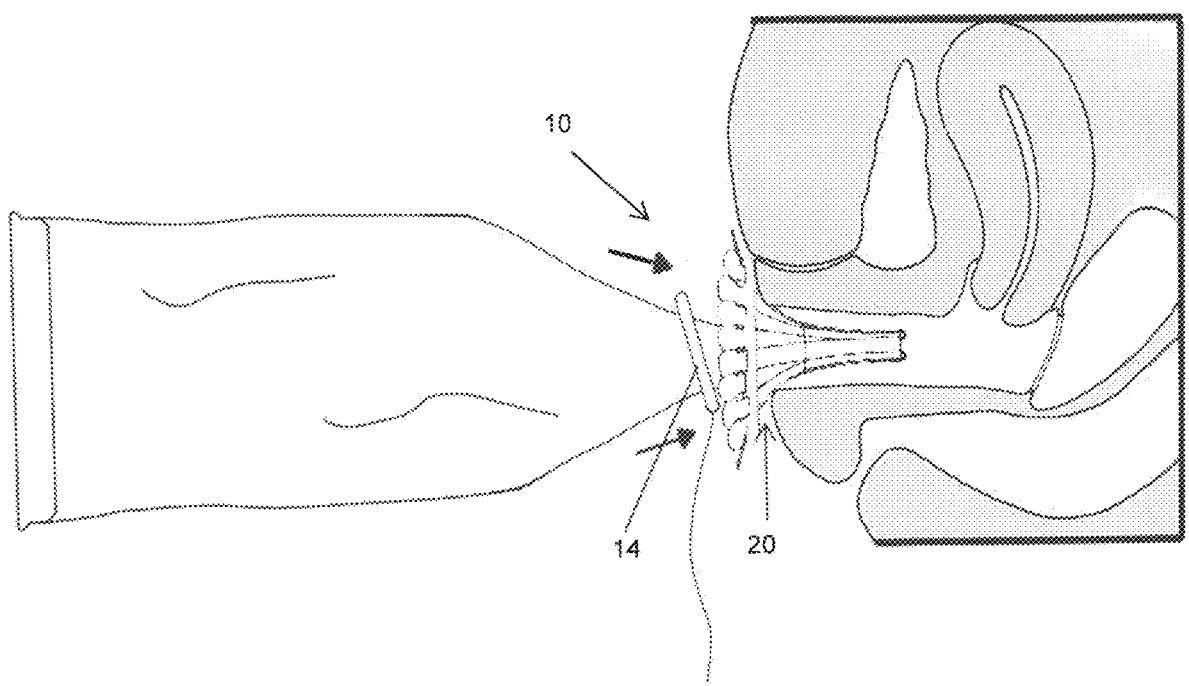
FIGS. 23A, 23B, and 23C are views illustrating the insertion of the medical device of FIG. 1A into a body opening according to an embodiment.
Figure 23B:
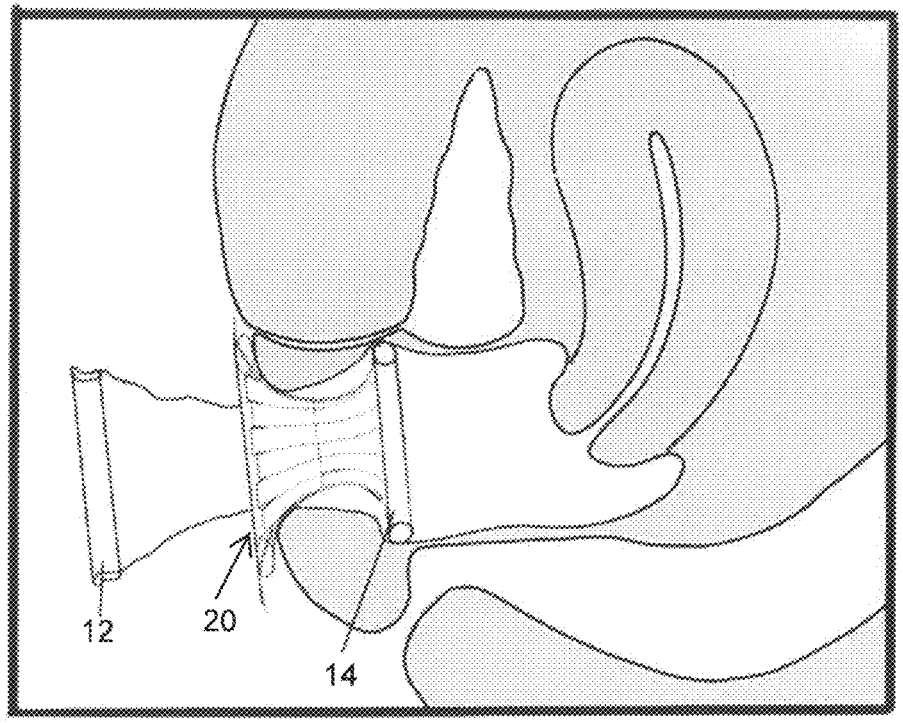
Figure 23C:
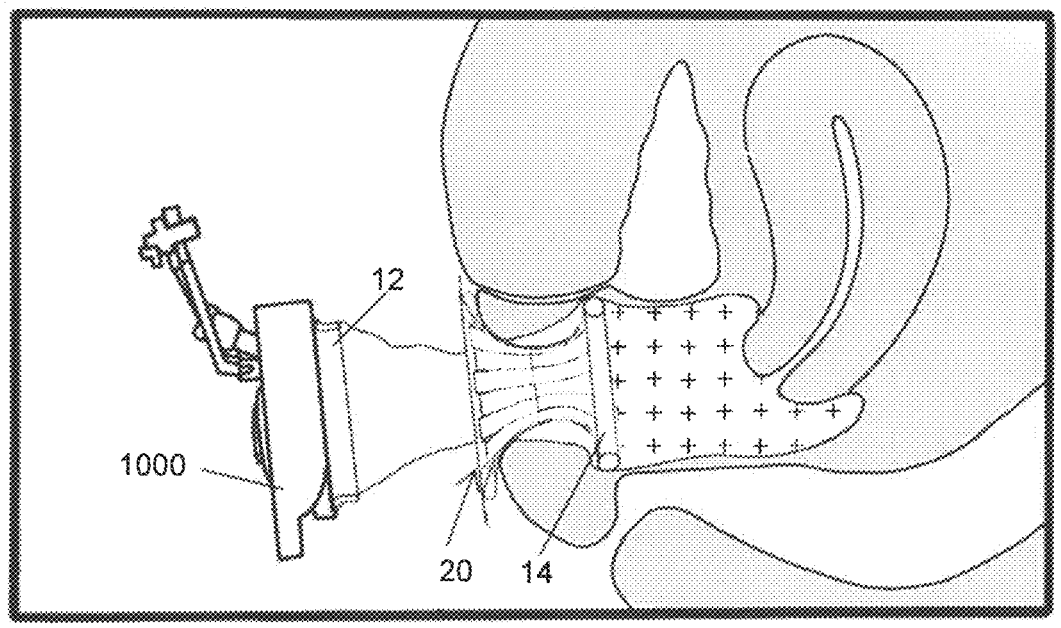

Insertion of medical device 10 into another body opening, e.g., a vaginal opening, is shown in FIGS. 23A-23C. For example, guard assembly 20 may be inserted into a vaginal opening and distal ring 14 may be subsequently inserted into the vaginal opening as shown in FIG. 23A. With reference to FIG. 23B, distal ring 14 may be seated within a body cavity against the tissue surrounding the vaginal opening. Guard assembly 20 may expand as proximal 12 is rolled toward the vaginal opening. As shown in FIG. 23C, a cap (such as cap 1000 in FIG. 18A, or any cap described herein) may be attached to proximal ring 12. The cap may facilitate insertion of medical tools and/or may aid in performing medical procedures. Additionally, or alternatively, the cap may facilitate insufflation and/or desufflation of the body cavity, e.g., by preventing or releasing gas from the cavity during a medical procedure.

Figure 12:
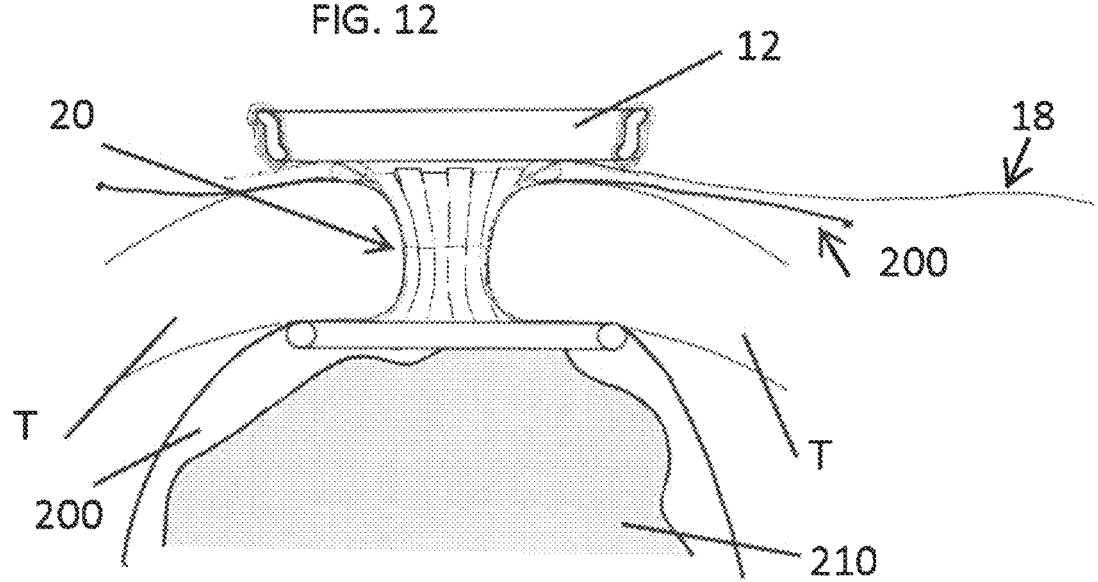
FIG. 12 is a view illustrating the use of the medical device of FIG. 1A with an auxiliary medical device.

Alternatively, or additionally, one or more devices may be inserted through opening 100 prior to inserting medical device 10. For example, as shown in FIG. 12, a tissue containment bag 200 may be inserted into opening 100 prior to inserting medical device 10. Containment bag 200 may be used for any medical procedure, e.g., a morcellation procedure on a tissue sample 210. After containment bag 200 is inserted via opening 100 and tissue sample 210 is disposed within containment bag 200, medical device 10 may be inserted into opening 100 in the manner described herein. In this manner, when guard assembly 20 is "locked" within opening 100, petals 30 may protect both tissue T within opening 100 and containment bag 200 extending through opening 100, as shown in FIG. 12. Thus, in the event a morcellation, such as a manual morcellation using a sharp instrument, or any other procedure is performed, petals 30 may protect containment bag 200 and/or tissue T within opening 100 from being cut or otherwise compromised.

Figure 11A:
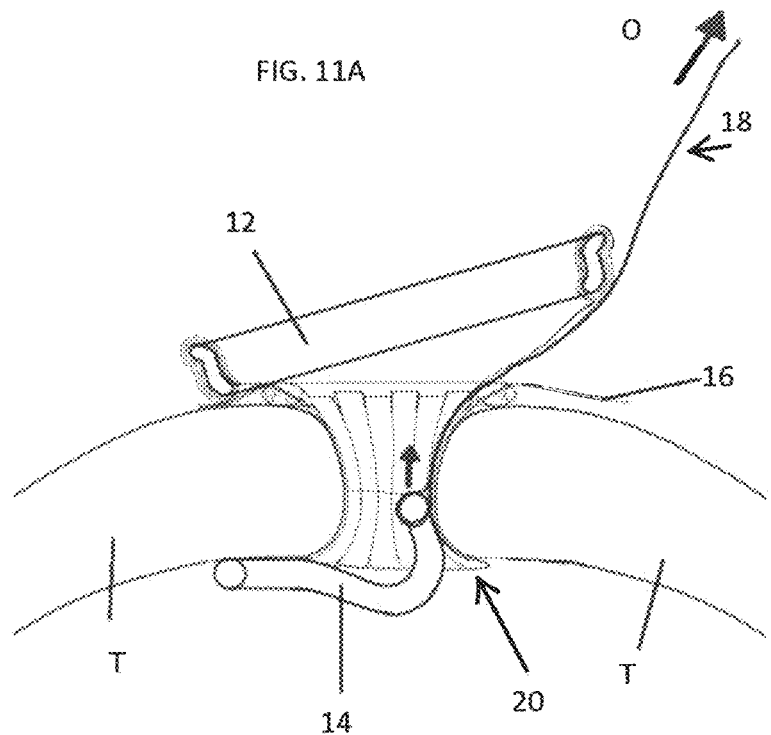
FIGS. 11A, 11B, and 11C are views illustrating a removal of the medical device of FIG. 1A into a body.
Figure 11B:
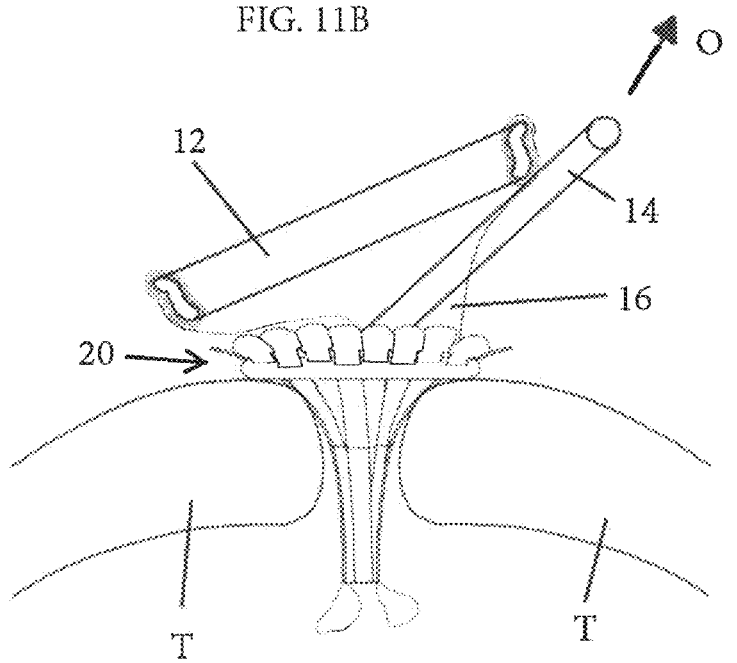
Figure 11C:
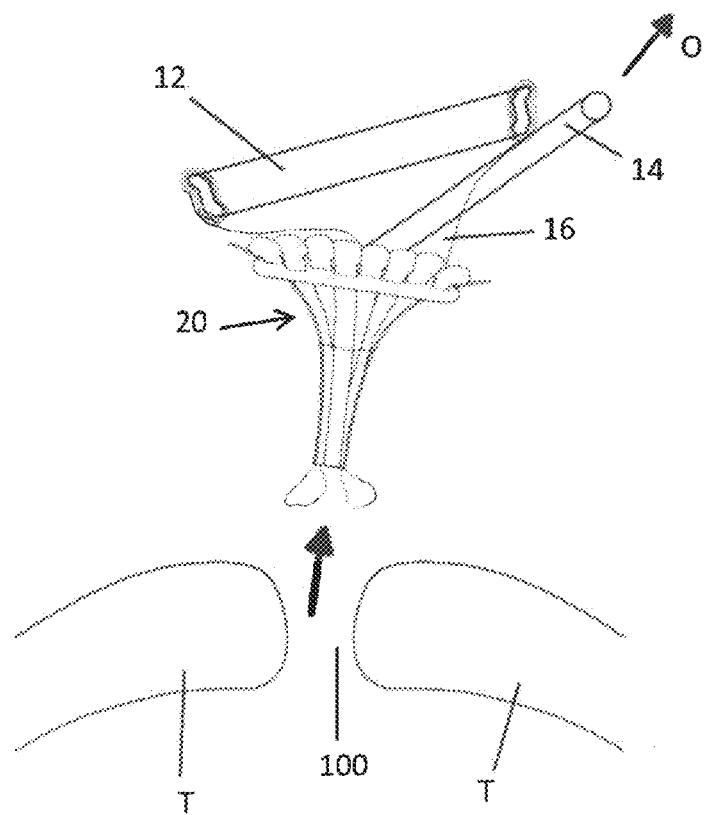

Once the medical procedure is complete, medical device 10 may be removed from opening 100 as shown in FIGS. 11A-11C. For example, a user may grasp tether 18 and move tether 18 in the proximal direction, indicated by arrow O. Such movement causes distal ring 14, which is attached to tether 18 at tether connection 18a (see FIG. 1A), to fold or deform and move proximally through opening 100. Once distal ring 14 is pulled proximally through opening 100, the access device 10 can be easily pulled out from body opening 100. In this manner, movement of tether 18 in the proximal direction removes medical device 10 from opening 100. In the event another medical device (e.g., containment bag 200) was inserted prior to medical device 10, the other medical device may then be removed through opening 100.

Access device 10 may thus provide a single device for both retraction and protection of a body opening 100. Further the overlapping petals 30 of guard assembly 20 allow for retraction and protection over a plurality of different retracted sizes of opening 100. In some instances, this may provide improved protection for small, vulnerable incisions, which may increase the protection of these vulnerable access openings. Access device 10 provides for ease of use by providing simultaneous insertion and removal of the retraction sleeve 16 and guard assembly 20, and simultaneous retraction of opening 100 and expansion of the guard assembly 20. Access device 10 may also provide protection for various body openings 100, e.g., different tissue (e.g., abdominal wall) thicknesses and different incision or orifice shapes and sizes since access device 10 is self-adjusting. Further, access device 10 may provide protection to the tissue surround a body opening 100 inside and outside the body, as well as the walls or tissue within the opening. In addition, distal ring 14 may anchor access device 10 and may provide additional protection to a bag or other device inserted through the body opening by, for example, providing an additional securement of the bag or device, and/or urging the bag or device farther away from the body opening 100.

According to an example, manual morcellation in containment bag 200 may be desired for certain types of tissues, e.g., tissues that may be exposed to cancers, benign growths, and/or other pathogens. Performing these procedures in containment bag 200 may prevent the spread of the pathogens through a body as the tissue is morcelated. However, using a scalpel and/or forceps during morcellation may damage containment bag 200 such as at a location near the opening in the body (e.g., incision, natural orifice, etc.) through which containment bag 200 is extended. Damaging containment bag 200 may be a critical failure in the procedure, as it may allow pathogens to spread throughout the body. In another example, inserting medical instruments or tools, e.g., a knife, grasping mechanism, or the like, may damage tissue at a location near the opening in the body (e.g., incision, natural orifice, etc.). Medical device 10 may provide a barrier between (1) the medical instruments or tools and (2) containment bag 200 and/or tissue at the opening of the body through which the medical instruments or tools are inserted.

Figure 14A:
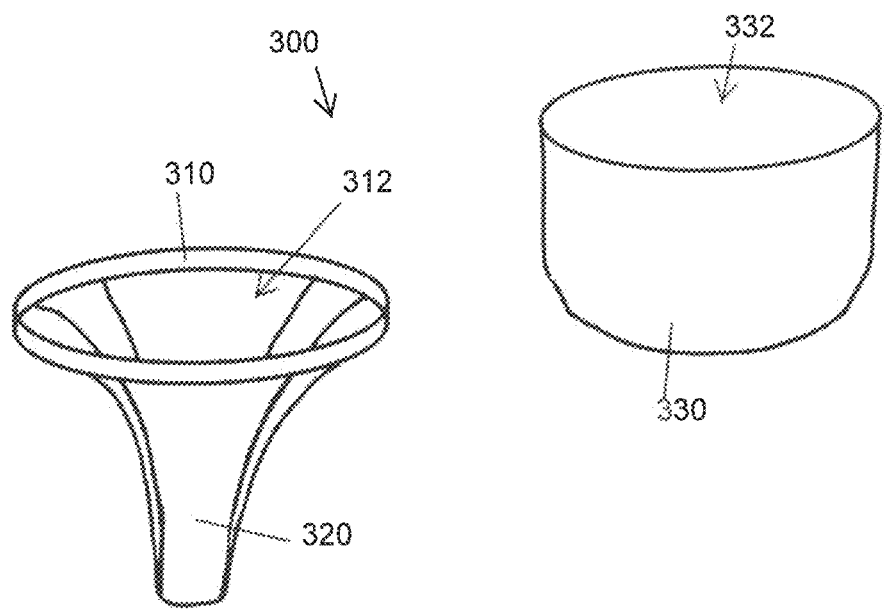
FIGS. 14A, 14B, 14C, 14D, and 14E are views illustrating a medical device according to an embodiment.
Figure 14B:
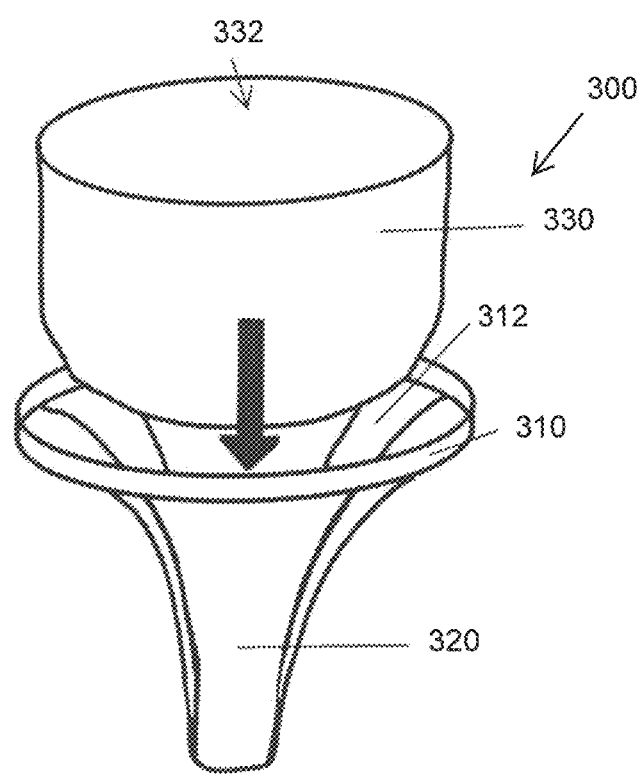

An access device 300 according to another embodiment is shown in FIGS. 14A-14E. Access device 300 may include a guard 300 including guard ring 310 with one or more guard elements 320 extending therefrom. Guard ring 310 may be an annular device having an opening 312. Guard elements 320 may be attached at a first end to guard ring 310 via a hinge, an area having a reduced amount of material, or other mechanism for hingedly connecting guard elements 320 to guard ring 310. Guard elements 320 may be curved along their length, as shown in FIGS. 14A and 14B, or may be straight (not shown). Guard elements 320 may also be tapered from the end connected to guard ring 310 to an opposite end. This may enable guard elements 320 to approach and/or contact each other in an insertion configuration, shown in FIG. 14B.

Figure 14C:
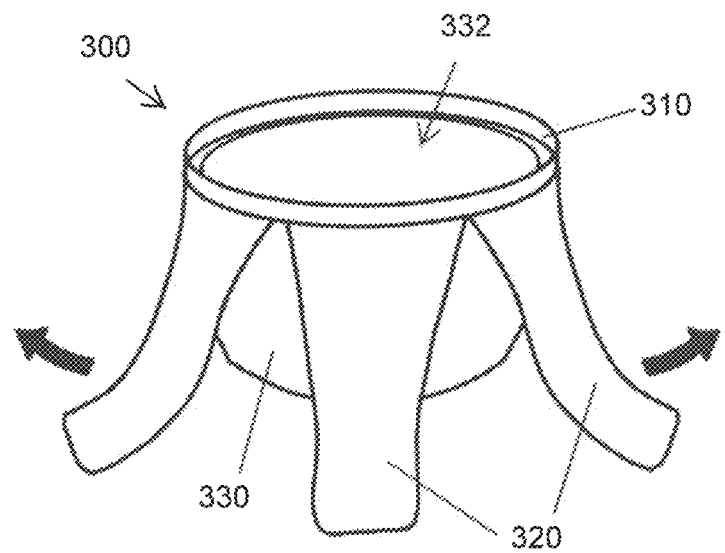

An insert 330 may be inserted into opening 312 and may urge or move guard elements 320 radially outward from the insertion configuration of FIG. 14B to a protection configuration shown in FIG. 14C. In the protection configuration, guard elements 320 may be urged radially outward by (1) insert 330, (2) a material of guard elements 320 (e.g., a shape memory material), and/or a spring or biasing mechanism (not shown) attached to guard elements 320 and guard ring 310. Guard elements 320 may secure access device 300 in an insertion opening (e.g., an incision or a natural orifice). Insert 330 may have an outer wall defining an opening 332. Opening 332 may allow instruments, body tissue, and/or other materials or tools to pass from an outside of the body into the body cavity during a medical procedure. Insert 330 may be formed of a material that is tear resistant and may protect tissue surrounding the insertion opening and/or a bag inserted into the insertion opening from being cut, torn, or otherwise breached by a medical tool during a medical procedure.

Figure 14D:
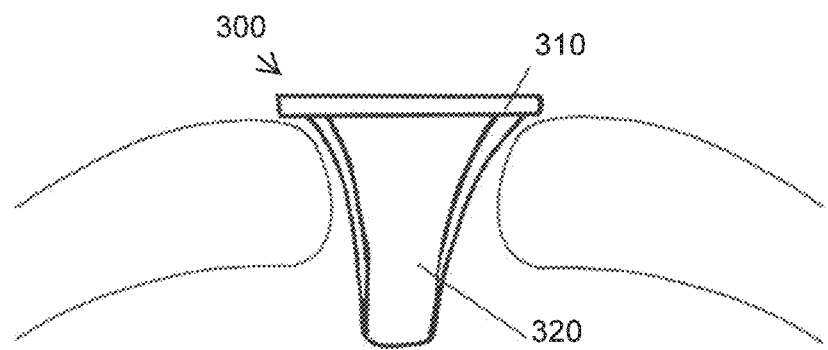
Figure 14E:
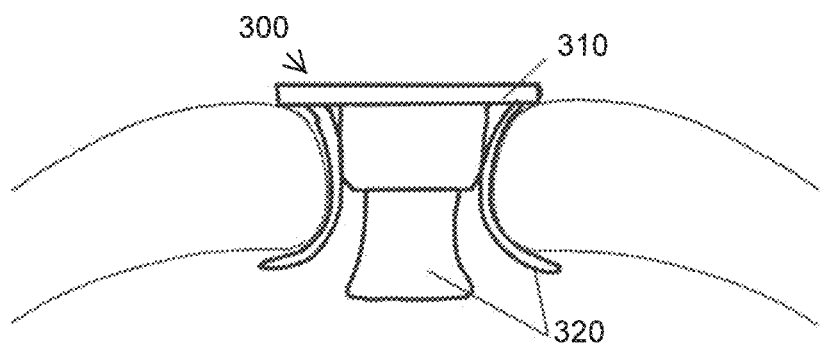

A method of inserting access device 300 will now be described. Guard ring 310 may be inserted into an opening in a body such that guard elements 320 extend into the body and guard ring 310 is positioned against an outer surface of the body, as shown in FIG. 14D. The opening may be an incision or any natural orifice (e.g., anus, vagina, etc.). Once access device 300 is properly positioned in the opening, insert 330 may be inserted into opening 312 of guard ring 310 and moved toward a body cavity. This may cause guard elements 320 to move radially outward, as shown in FIG. 14E. Guard elements 320 may contact tissue along the opening in the body and/or on an inner surface of a body cavity. This may secure access device 300 in the opening. Medical tools may be inserted through opening 332 to access a target site and perform a medical procedure. Once a medical procedure is complete, insert 330 may be removed from opening 312. Removing insert 330 may cause guard elements 320 to move radially inward. Distal ring 310 may then be pulled outward away from the opening, such that guard elements 320 may be pulled from the opening.

An access device 400 according to another embodiment is shown in FIG. 15A-15D. Access device 400 may include a proximal ring 410, a distal ring 420, and a plurality of straps 430 connecting proximal ring 410 to distal ring 420. Straps 430 may be connected at a first end to distal ring 420 in a fixed manner. For example, straps 430 may extend into openings in distal ring 420, or straps 430 may be looped around distal ring 420 to connect thereto.

Figure 15D:
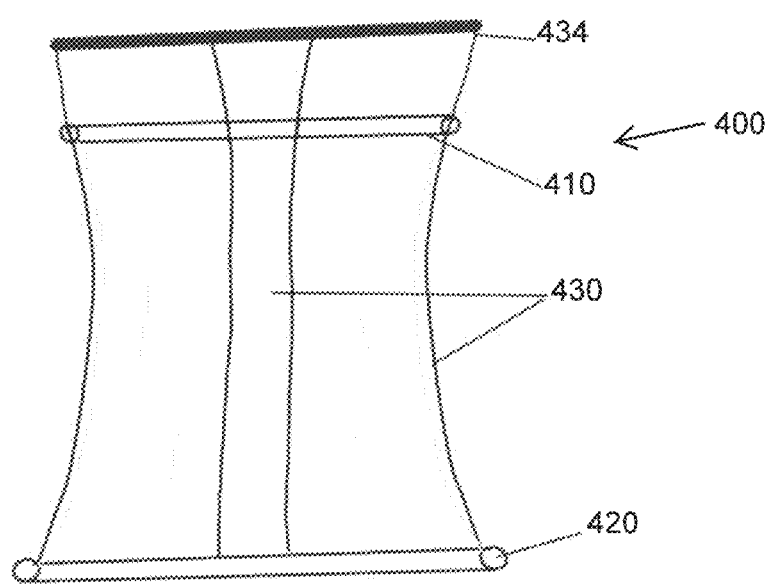

Straps 430 may include ridges 432 (e.g., protrusions) along one side of each strap 430, as shown in FIG. 15B. Straps 430 may extend from distal ring 420 through corresponding slots 412 in proximal ring 410. Each slot in proximal ring 410 may include a protrusion 412a which may engage ridges 432 of straps 430. For example, protrusion 412a may be disposed between two adjacent ridges 432. To move strap 430 relative to proximal ring 410, a force may be applied to strap 430 sufficient to overcome a force supplied by protrusion 412a and ridges 432 to maintain a position of strap 430 to proximal ring 410. For example, this may provide a friction lock or may be a ratchet-type device. Pulling straps 430 in the direction indicated by arrow Q in FIGS. 15A and 15B and/or pushing proximal ring in the direction indicated by arrow R in FIG. 15C may cause a distance between proximal ring 410 and distal ring 420 to be reduced. To increase the distance between distal ring 420 and proximal 410, proximal ring 410 may be moved away from distal ring 420. In some instances, a strap ring 434 may be attached to an end of each strap 430 opposite distal ring 420 (FIG. 15D). Strap ring 434 may enable a user to move all straps 430 at a same time. While four straps 430 are shown in the drawings, it will be understood that any number of straps 430 may be provided, for example, two, three, five, or more.

In some instances, straps 430 may be used to protect tissue of an opening through which a medical procedure may be performed. Alternatively, or additionally, a guard (such as those devices used with medical access devices 10 and/or insert 330 of FIG. 14A) may be used with access device 400. For example, a guard device may be inserted into an opening formed in proximal ring 410 and distal ring 420 and may protect tissue as described herein. For example, access device 400 may be inserted into an opening and straps 430 may be adjusted to position proximal ring 410 and distal ring adjacent tissue defining the opening. In some instances, a bag may be positioned in the body opening, and access device may be positioned within the bag, such that the bag is positioned between access device 400 and the tissue defining the body opening. An insert, such as insert 330, may be positioned within an opening defined by proximal ring 410 and an opening defined by distal ring 420. Insert 330 may prevent instrument from damaging the tissue wall and/or a bag positioned radially outward of access device 400 during a medical procedure. Alternatively, a guard may be positioned within the body opening, and access device 400 may be positioned within an opening of the guard. Tightening straps 430 may maintain a position of the guard within the body opening.

A method of inserting access device 400 will now be described. Distal ring 420 may be inserted into an opening, e.g., an incision or a natural orifice (anus, vagina, etc.), such that the distal ring 420 is seated within a body cavity. Straps 430 may subsequently pulled outward from the body, e.g., in a proximal direction. In some instances, proximal ring 410 may be simultaneously moved toward the opening in the body, e.g., in a distal direction indicated by arrow R in FIG. 15C. This movement may cause straps 430 to move within corresponding slots 412 such that ridges 432 move past protrusions 412a. In some cases, strap ring 434 may be moved proximally, which may cause all straps 430 to move simultaneously.

Once proximal ring 410 is seated against an outer surface of the body, a user may insert tools through an opening in proximal ring 410 and distal ring 420 to access a target site with in the body. In some instances, a guard (such as those guards used with access device 10) may be inserted into the opening to provide additional protection against tools during the medical procedure. Once the procedure is complete, access device 400 may be removed from the opening. In some instances, proximal movement of access device 400 may cause distal ring 420 to be moved outside the opening.

Alternatively, proximal ring 410 may be moved proximally relative to straps 430 to provide slack between proximal ring 410 and distal ring 420. Once a sufficient slack in straps 430 is achieved, distal ring 420 may be pulled from the opening.

FIGS. 16A-J illustrate various embodiments of designs for a distal ring, such as distal ring 14 in FIG. 1. With reference to FIG. 16A, distal ring 14 may include a single annular ring with a circular cross-section. It will be understood that the cross-section is not limited thereto, and may be ovular, rectangular, or the like.

FIG. 16B illustrates another example of a distal ring 114. Distal ring 114 may include two distal rings 114a, 114b stacked one on top of the other, e.g., stacking two distal rings 14, connected together via a piece of material 114c. In some instances, distal rings 114a, 114b may be formed as a unitary piece, e.g., via extrusion. FIG. 16C illustrates another example of a distal ring 214 in which three distal rings 214a, 214b, 214c are stacked together. Adjacent distal rings 214a, 214b, 214c may be connected via material 214d. As with distal ring 114, distal ring 214 may be formed as a unitary piece.

FIG. 16D illustrates an example of a distal ring 314 including a plurality of stacked rings 314a. Adjacent rings 314a may include diameters different from each other such that distal ring 314 may be funnel-shaped. As with distal rings 14 and 114, adjacent rings 314a may be connected via material between each adjacent ring 314a and/or distal ring 314 may be formed as a unitary member. The funnel-shaped design of distal ring 314 may allow the shape of distal ring 314 to be selected by a physician based, e.g., based on the type of procedure being performed, the size of the opening, and/or a patient-specific anatomy. In some instances, the physician may cut distal ring 314 at one or more locations to select the size of distal ring 314.

FIG. 16E illustrates a distal ring 414 having an ovular cross-section, which may increase a stability and a sealing surface of an access device within the body. As another example, FIG. 16F illustrates a distal ring 514 having a C-shaped cross section, which may improve the stability and/or the grip of distal ring 514 within the opening. This may provide a better seal between the access device and the opening, e.g., by seating the access device against the opening.

A distal ring 614 having an elongated outer surface with a V-shaped region near its center is shown in FIG. 16G. Distal ring 614 may be compressed and/or may expand via the V-shaped region to provide improved sealing between the opening and the access device.

FIG. 16H illustrates a distal ring 714, which may expand from a generally circular shape to a generally ovular shape, as shown by arrows Z. This configuration may allow distal ring 714 to have a reduced cross-sectional area during insertion to the body, which may allow distal ring 714 to fit through smaller body openings. Once inserted into the body, distal ring 714 may expand to provide a larger cross-sectional area which may provide increased rigidity to an access device during a procedure.

FIGS. 16H and 16I illustrate distal rings 814 and 914, respectively, which may have an inflation portion. Distal ring 814 has a generally circular cross-section, similar to that of distal ring 14. A radially outer surface 814a of distal ring 814 include an inflatable member 814b, which may be inflated or deflated to provide additional sealing and support between the access device and the body. Distal ring 914 may be V-shaped, e.g., similar to distal ring 614, and may include an inflatable member 914a positioned generally in the V-shaped region. Similar to inflatable member 814a, inflatable member 914a may be inflated or deflated and may provide improved sealing or support to an access device.

Figure 17A:
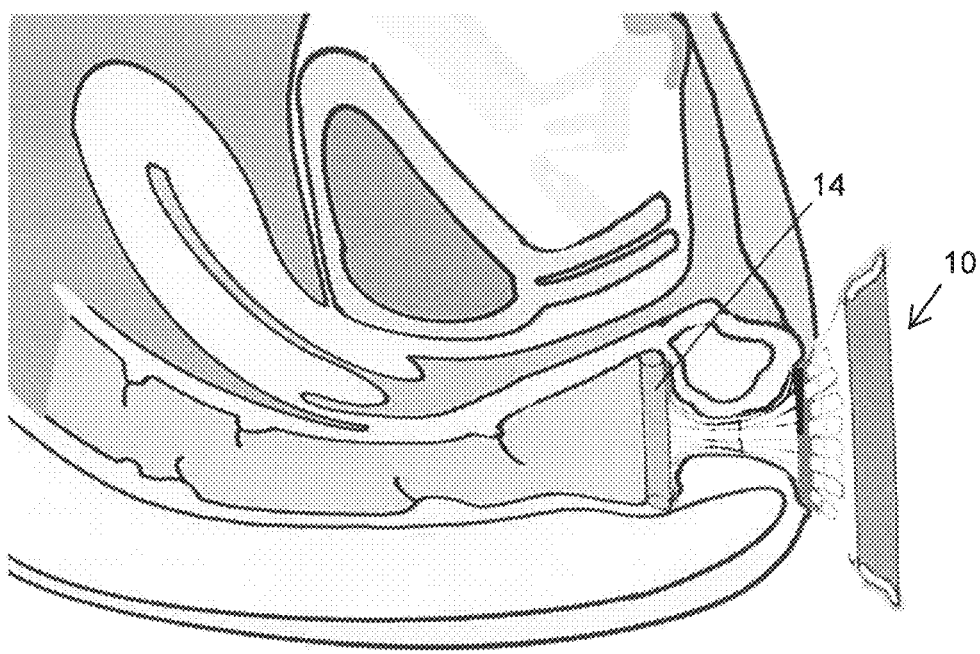
FIGS. 17A and 17B are views illustrating the insertion of the medical device of FIG. 1A into a body opening according to an embodiment.
Figure 17B:
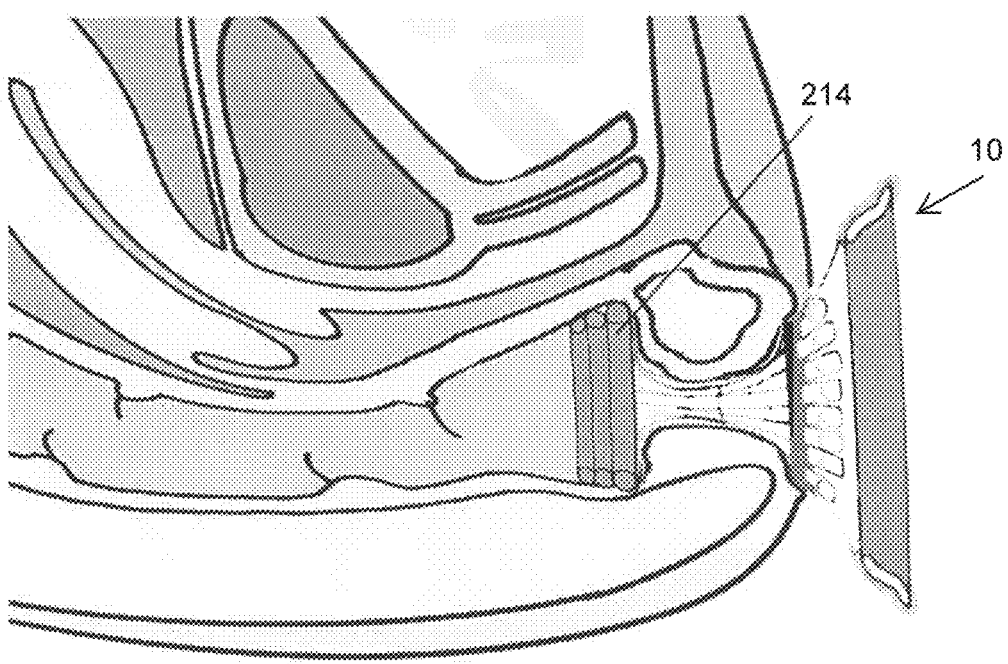

FIGS. 17A and 17B illustrate examples of distal rings positioned within a body opening. FIG. 17A illustrates a distal ring, e.g., distal ring 14, positioned within a natural orifice of the patient, with an access device, e.g., access device 10, protruding through the opening. FIG. 17B illustrates a distal ring, e.g., distal ring 214 or distal ring 314, which has may have been sized to fit the patient-specific anatomy. An access, device, e.g., access device 10, may protrude from the natural opening. The various shapes, sizes, and functionalities (e.g., inflation, deflation) of the distal rings may provide improved sealing and/or positioning of an access device within the body.

Figure 18A:
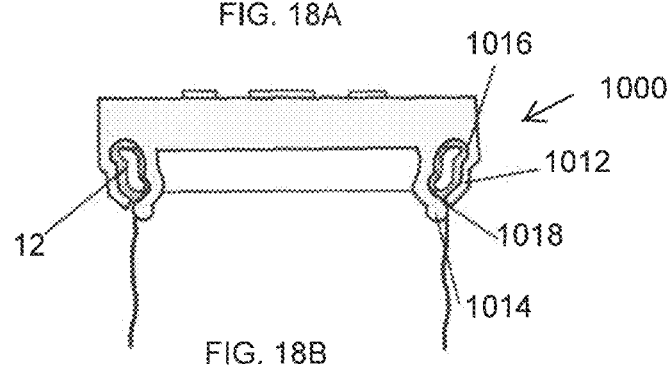
FIGS. 18A and 18B are views illustrating a cap according to an embodiment.
Figure 18B:
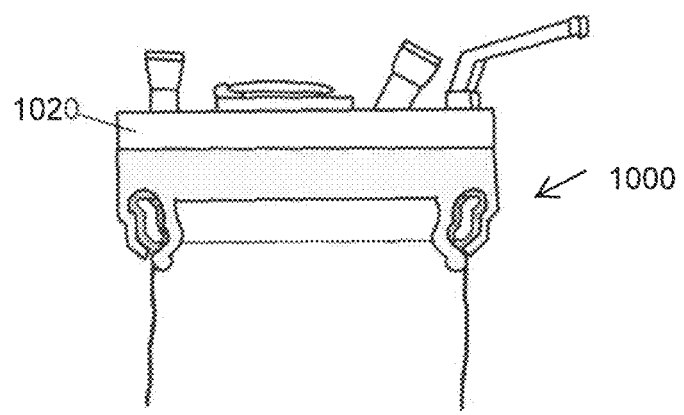

FIGS. 18A and 18B illustrate a cap 1000 which may be clipped onto a proximal ring of an access device, e.g., proximal ring 12 of access device 10 of FIG. 1. Cap 1000 may include an annular member 1010 extending from a first surface 1000a of cap 1000. Annular member 1010 may include an outer annular wall 1012 and an inner annular wall 1014. An annular lumen 1016 may be defined between outer annular wall 1012 and inner annular wall 1014. One or both of outer annular wall 1012 and inner annular wall 1014 may be capable of bending or being deformed. An opening 1018 may be formed between outer annular wall 1012 and inner annular wall 1014 when outer annular wall 1012 and inner annular wall 1014 are deformed, which may allow access to annular lumen 1016. This may allow cap 1000 to be clipped or otherwise attached to proximal ring 12. For example, as shown in FIG. 18A, proximal ring 12 may fit within annular lumen 1016 such that cap 1000 may be secured to access device 10. In some examples, cap 1000 may include one or more ports through which medical instruments, air, water, or other items may be introduced or removed during a medical procedure. It will be understood that the one or more ports may be attached to a port device 1020, as shown in FIG. 18B, and may be attached to cap 1000 via a screw fit, clip, snap fit, or the like.

Figure 19:
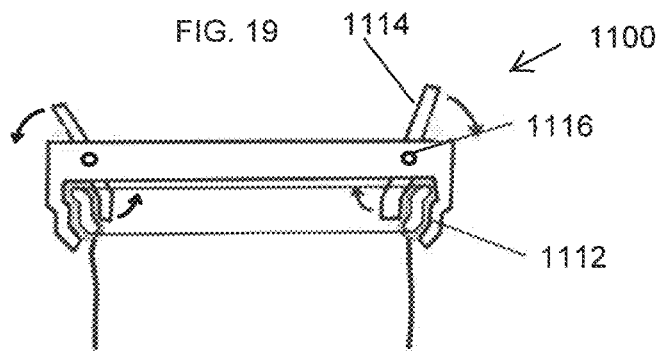
FIG. 19 is a view illustrating a cap according to another embodiment.

A cap 1100 according to another example is shown in FIG. 19. Cap 1100 may have an outer annular wall 1112 and one or more levers 1114 hingedly attached to cap 1100 via one or more pivot points 1116. Levers 1114 may pivot between an open position and a closed position (the closed position shown in FIG. 19). Outer annular wall 1112 may be placed such that it is radially outward from proximal ring 12. Levers 1114 may be moved from the open position to the closed position, where a portion of levers 1114 contact proximal ring 12. In some instances, levers 1114 may push or urge proximal ring 12 against an inner surface of outer annular wall 1112. In an example, levers 1114 may be biased via a biasing member (e.g., a spring) in the closed position. To remove cap 1100, levers 1114 may be pivoted about pivot point 1116 to the open position, and cap 1100 may be removed from proximal ring 12.

Figure 20A:
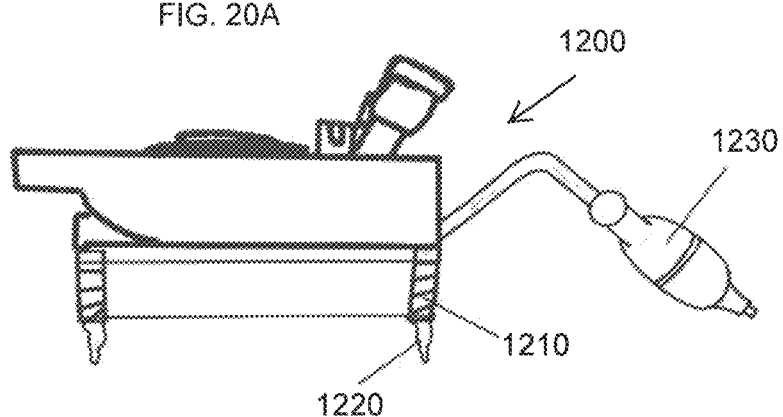
FIGS. 20A and 20B are views illustrating a cap according to another embodiment.
Figure 20B:
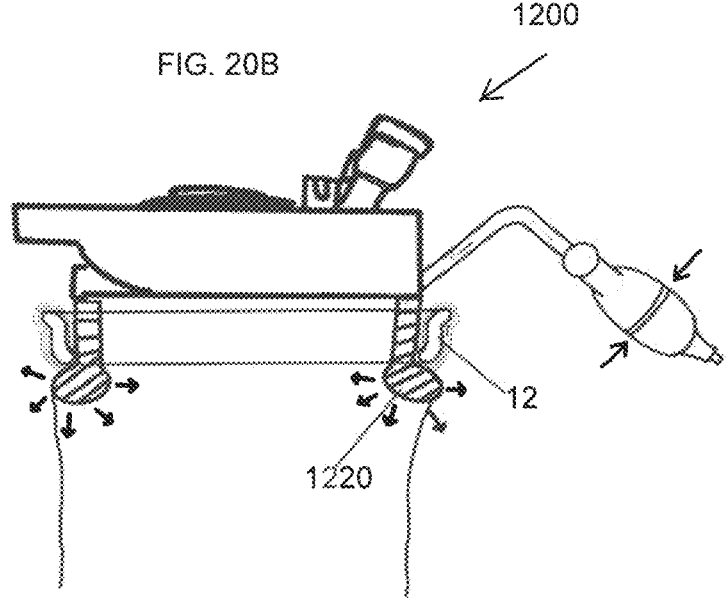

A cap 1200 according to another example is shown in FIGS. 20A and 20B. Cap 1200 may include an annular wall portion 1210 extending form cap 1200 and may include an inflatable member 1220, e.g., a balloon, attached to an end of annular wall portion 1210. An inflation mechanism 1230, e.g., a pump device or tube configured to attach to an air supply, may be attached to cap 1200. Annular wall portion 1210 may be inserted into an opening defined by proximal ring 12. Inflatable member 1220 may then be inflated via inflation mechanism 1230. Inflatable member 1220 may inflate and secure cap 1200 to an inner surface of proximal ring 12. To remove cap 1200, air may be released from inflatable member 1220 and cap 1200 may be removed from the opening of proximal ring 12.

A cap 1300 according to an example is shown in FIG. 21. A sleeve 1310 may extend from sleeve 16 in a proximal direction, e.g., away from a body opening, at a location where proximal ring 12 is attached to sleeve 16. Sleeve 1310 may include a proximal ring 1320 which may be flexible. Cap 1300 may fit within an opening of proximal ring 1320. Sleeve 1310 may move proximally and distally as proximal ring 12 is rolled or unrolled.

Figure 22A:
FIGS. 22A, 22B, and 22C are views illustrating a cap according to another embodiment.
Figure 22B:
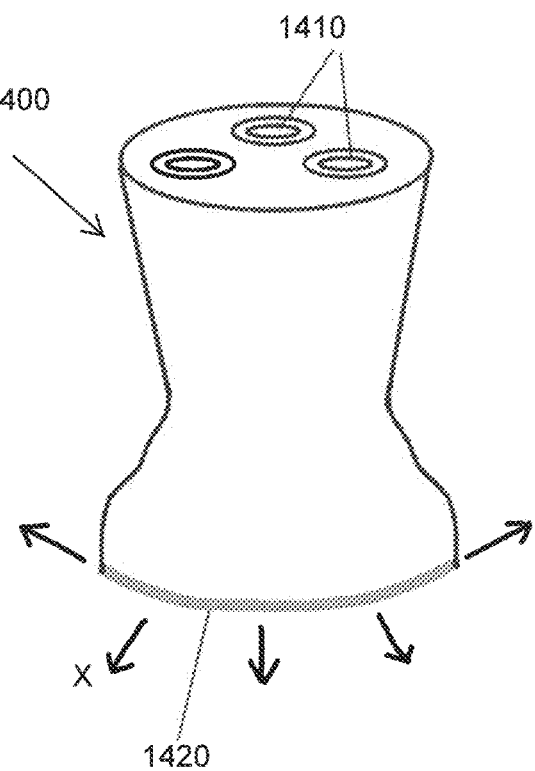
Figure 22C:
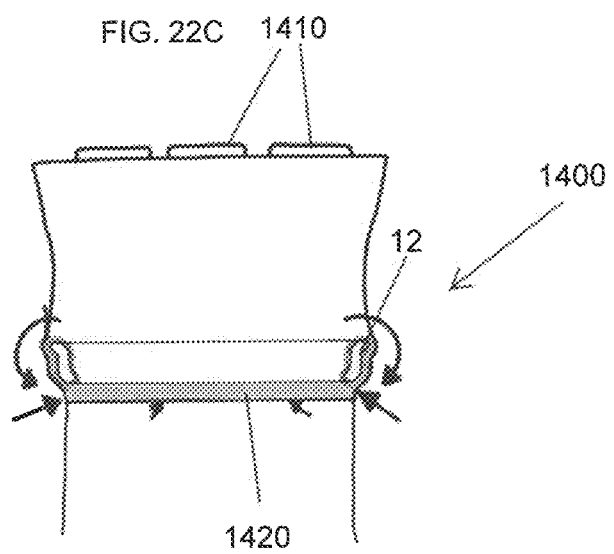

A cap 1400 according to an example is shown in FIGS. 22A, 22B, and 22C. Cap 1400 may include an elastic sleeve having a plurality of ports 1410 at a first end and an opening 1420 at an opposite end as shown in FIGS. 22A and 22B. The material of cap 1400 at opening 1420 may stretch or expand as indicated by arrows X in FIGS. 22A and 22B. Opening 1420 may be placed over proximal ring 12 and the material may contract or be released to contact proximal ring 12 as shown in FIG. 22C. This may allow cap 1400 to be sealed to proximal ring 12 of an access device (e.g., access device 10 in FIGS. 1A and 1B). Ports 1410 may allow access to medical instruments, while maintaining a fluid seal e.g., to prevent bodily materials and/or fluids from escaping through an opening in the access device.

It will be understood that, unless specifically set forth herein, any material known in the art may be used for the various elements. For example, features may include a medical grade plastic or rubber, a ceramic, a metal, or a combination thereof.

It will be apparent to those skilled in the art that various modifications and variations can be made to the disclosed device without departing from the scope of the disclosure. For example, the configuration of petals arranged radially about the guard may change in size and number, based on a size of an opening in the body to be accessed. In other examples, the distal ring may be fixedly attached to a portion of the sleeve or the guard 20. Various components of the medical access device may be changed based on the size and/or location of the body opening, and/or the medical procedure to be performed via the body opening. Further, embodiments allow different auxiliary medical devices to access the body via the body opening, while protecting tissue of the body opening and/or the auxiliary medical devices at least at the body opening. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device configured to protect a body opening, the medical device comprising:
    a sleeve having a proximal end and a distal end;
    a proximal ring attached to the proximal end of the sleeve; and
    a guard assembly located at the distal end of the sleeve, the guard assembly including:
        a plurality of elongated members; and
        a guard ring having a plurality of apertures;
        when the medical device is in the body opening, retraction of the sleeve causes the plurality of elongated members to move through the guard ring.

2. The device of claim 1, wherein a portion of each of the plurality of elongated members is secured to the distal end of the sleeve.

3. The device of claim 2, wherein the distal end of the sleeve includes a plurality of pockets, and wherein each of the elongate members is secured within a corresponding pocket of the plurality of pockets.

4. The device of claim 1, wherein a portion of the sleeve extends proximally through a central aperture of the guard ring.

5. The device of claim 1, further comprising a distal ring, wherein the distal ring is movable relative to the sleeve and the guard assembly, and wherein the distal ring is movable to a position distal to a distal-most end of the guard assembly.

6. The medical device of claim 1, wherein the sleeve and the guard assembly are separate components configured to attach to one another.

7. A medical system configured to protect a body opening, the medical system comprising:
    a retractor sleeve having a proximal end and a distal end, a proximal retractor ring and a distal retractor ring; and
    a guard assembly located at the distal end of the sleeve in a deployed configuration, wherein the guard assembly includes a guard ring and a plurality of petals, wherein the guard ring includes a plurality of apertures, wherein one petal from the plurality of petals is disposed within a corresponding aperture of the plurality of apertures, wherein the plurality of petals are movably connected to the guard ring and when the medical device is in the body opening, retraction of the sleeve causes the plurality of petals to move through the guard ring.

8. The system of claim 7, wherein a portion of the sleeve extends through a central opening of the guard ring.

9. The system of claim 7, wherein the retractor sleeve and the guard assembly are separate component configured to attach to one another.

10. A medical device configured to protect a body opening, the medical device comprising:
    a sleeve having a proximal end and a distal end;
    a guard assembly having a guard ring and a plurality of petals; and
    a plurality of pockets formed at the distal end of the sleeve, wherein each petal of the plurality of petals is secured within a corresponding pocket of the plurality of pockets; wherein retraction of the sleeve causes the plurality of petals to move through the guard ring.

11. The medical device of claim 10, wherein a width at a distal end of each petal is less than a width of each petal at the proximal end, and wherein a connection member in each of the plurality of pockets cooperates with the distal end of a corresponding petal to fix the petal into the corresponding pocket.

12. A medical device configured to protect a body opening in a deployed configuration, the medical device comprising:
    a sleeve having a proximal end and a distal end;
    a proximal ring attached to the proximal end of the sleeve;
    a guard assembly including a guard ring and a plurality of petals located at the distal end of the sleeve, when the medical device is in the body opening, retraction of the sleeve causes the plurality of petals to move through the guard ring; and
    a distal ring, wherein the distal ring is movable relative to the sleeve and the guard assembly, and wherein the distal ring is disposed at a distal-most end of the guard assembly in the deployed configuration.

13. The device of claim 12, wherein the distal ring is configured to be moved between a first position, in which at least a portion of the distal ring is disposed outside the body, and a second position, in which the distal ring is disposed within the body.

14. The device of claim 12, wherein a portion of the sleeve is received within the distal ring.

15. A method of retracting a body opening, the method comprising:
   inserting a medical device into the body opening, the medical device including a sleeve, a proximal ring attached to a proximal end of the sleeve, a guard assembly attached to a distal end of the sleeve, and a distal ring;
   moving the distal ring from a first position, wherein at least a portion of the distal ring is disposed outside the body, to a second position, in which the distal ring is disposed entirely inside the body; and
   moving the proximal ring distally to urge a portion of the sleeve and guard radially outwardly within the body opening;
   wherein the guard assembly includes a guard ring and a plurality of petals, and moving of the proximal ring moves the petals with respect to the guard ring.

16. The method of claim 15, wherein moving the proximal ring further includes rolling the proximal ring proximally to shorten a distance of sleeve between the proximal ring and the distal ring.

17. The method of claim 15, further comprising inserting an auxiliary device into the body opening before the medical device is inserted into the body opening.

18. A medical system configured to protect a body opening, the medical system comprising:
   a retractor sleeve having a proximal end and a distal end;
   a proximal ring retractor attached to the proximal end of the sleeve;
   a distal retractor ring received about a portion of the sleeve; and
   a guard assembly located at a distal end of the sleeve when in a deployed configuration, the guard assembly including:
      a guard ring;
      a plurality of petals movably coupled to the guard ring, the plurality of petals being configured to move with respect to the guard ring; and
      a guard sleeve including a plurality of petal pockets receiving the plurality of petals, wherein retraction of the retractor sleeve causes the plurality of petals to move through the guard ring.

19. The medical system of claim 18, wherein the retractor sleeve and the guard sleeve are integrally formed.

* * * * *